(12) United States Patent
Mayumi

(10) Patent No.: US 10,515,446 B2
(45) Date of Patent: Dec. 24, 2019

(54) IMAGE INSPECTION DEVICE, IMAGE INSPECTION METHOD, IMAGE INSPECTION PROGRAM, AND COMPUTER-READABLE RECORDING MEDIUM AND RECORDING EQUIPMENT

(71) Applicant: Keyence Corporation, Osaka (JP)

(72) Inventor: Norimasa Mayumi, Osaka (JP)

(73) Assignee: Keyence Corporation, Osaka (JP)

( * ) Notice: Subject to any disclaimer, the term of this patent is extended or adjusted under 35 U.S.C. 154(b) by 175 days.

(21) Appl. No.: 15/418,789

(22) Filed: Jan. 30, 2017

(65) Prior Publication Data

US 2017/0249727 A1    Aug. 31, 2017

(30) Foreign Application Priority Data

Feb. 26, 2016 (JP) ................................. 2016-036442

(51) Int. Cl.
*G06T 7/00* (2017.01)
*G01N 21/88* (2006.01)
(Continued)

(52) U.S. Cl.
CPC .......... *G06T 7/001* (2013.01); *G01B 11/0608* (2013.01); *G01B 11/24* (2013.01);
(Continued)

(58) Field of Classification Search
CPC .. G06T 7/001; G06T 7/74; G06T 7/60; G06T 5/006; G06T 7/248; G06T 7/11;
(Continued)

(56) References Cited

U.S. PATENT DOCUMENTS 6,919,577 B2 * 7/2005 Watanabe .............. B82Y 10/00
                                                          250/559.3
9,488,469 B1 * 11/2016 Michael ................. G01B 11/25
(Continued)

FOREIGN PATENT DOCUMENTS

| JP | 2006189315 A | 7/2006 |
| JP | 2015-031539 | 2/2015 |
| JP | 2015-031540 | 2/2015 |

*Primary Examiner* — Susan E. Hodges
(74) *Attorney, Agent, or Firm* — Kilyk & Bowersox, P.L.L.C.

(57) ABSTRACT

The image inspection device includes a reference height setting part configured to set a reference height as a reference of vibration component estimation, a vibration estimation part configured to estimate a vibration component in an inspection environment, based on the two-dimensional profile generated by the two-dimensional profile generation part and the reference height set by the reference height setting part, a profile correction part configured to remove, from the two-dimensional profile, the vibration component estimated by the vibration estimation part, a three-dimensional data generation part configured to generate three-dimensional data of the inspection object from a plurality of the two-dimensional profiles from which the vibration component is removed by the profile correction part, and an inspection part configured to conduct outer appearance inspection of the inspection object, based on the three-dimensional data generated by the three-dimensional data generation part.

18 Claims, 25 Drawing Sheets

(51) Int. Cl.
 G01B 11/24 (2006.01)
 G06K 9/00 (2006.01)
 H04N 13/00 (2018.01)
 H04N 13/204 (2018.01)
 G06T 7/73 (2017.01)
 G06T 7/11 (2017.01)
 G06T 7/246 (2017.01)
 G01B 11/06 (2006.01)
 G06K 9/62 (2006.01)
 G06T 5/00 (2006.01)
 G06T 7/60 (2017.01)
 H04N 5/225 (2006.01)
 G01N 21/84 (2006.01)

(52) U.S. Cl.
 CPC ....... *G01N 21/8851* (2013.01); *G06K 9/6215* (2013.01); *G06T 5/006* (2013.01); *G06T 7/11* (2017.01); *G06T 7/248* (2017.01); *G06T 7/60* (2013.01); *G06T 7/74* (2017.01); *H04N 5/2256* (2013.01); *H04N 13/204* (2018.05); *G01N 2021/845* (2013.01); *G01N 2201/12* (2013.01); *G06T 2200/08* (2013.01); *G06T 2207/30164* (2013.01)

(58) Field of Classification Search
 CPC ...... G06T 2200/08; G06T 2207/30164; H04N 13/204; H04N 5/2256; G06K 9/6215; G01B 11/0608; G01B 11/24; G01N 21/8851; G01N 2201/12; G01N 2021/845
 USPC ........................................................ 348/124
 See application file for complete search history.

(56) References Cited

U.S. PATENT DOCUMENTS 9,518,931 B2 * 12/2016 Kido ................... G01N 21/8851
2015/0022638 A1 * 1/2015 Saeki .................... G06T 7/0004
 348/46
2017/0248525 A1 8/2017 Mayumi

* cited by examiner

FIG. 4B
FIG. 4C
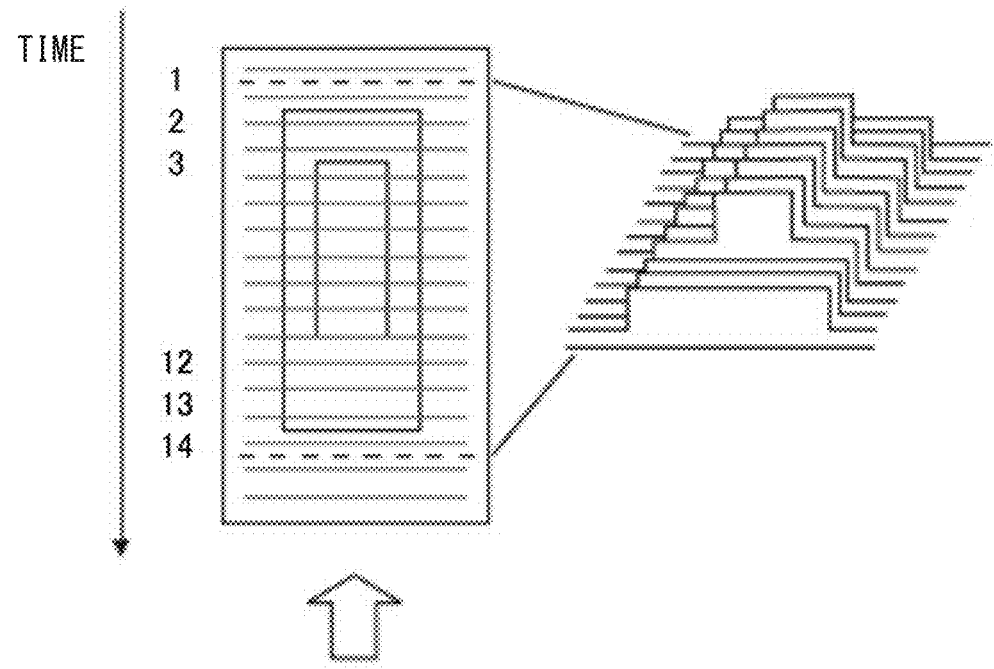
FIG. 4A
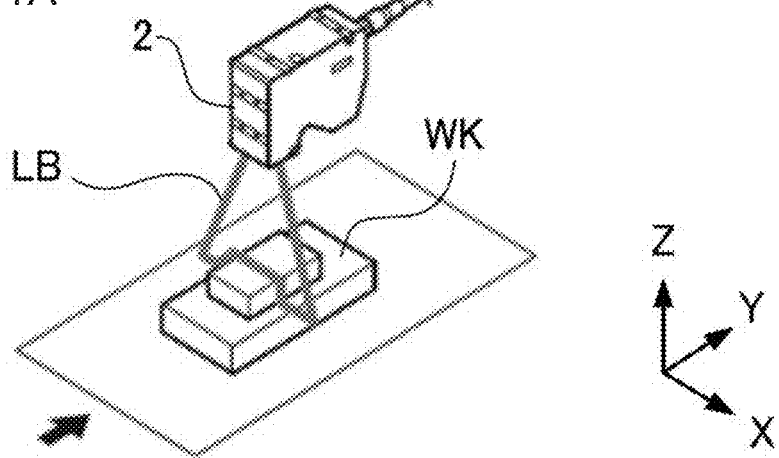

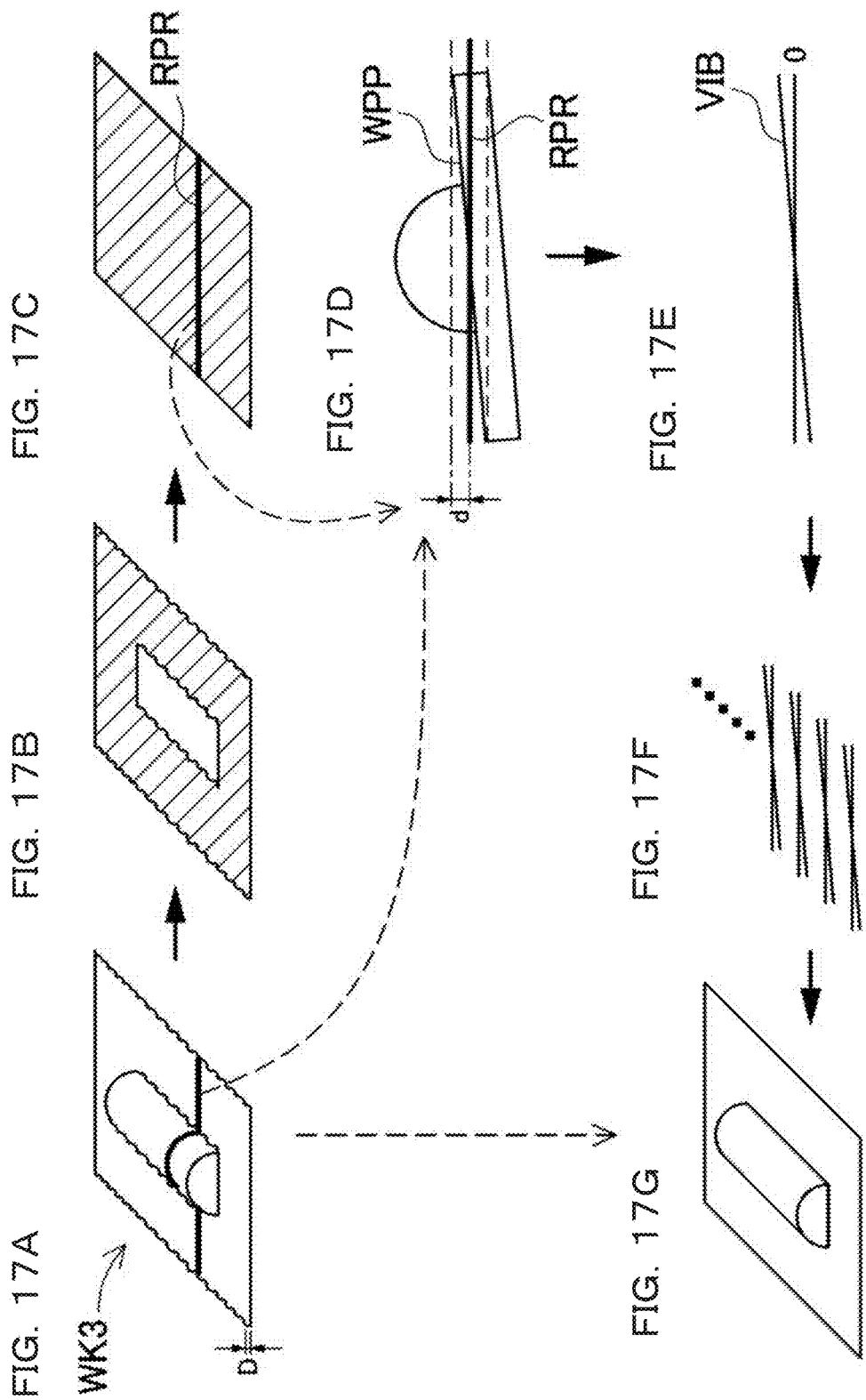

WK

IMAGE INSPECTION DEVICE, IMAGE INSPECTION METHOD, IMAGE INSPECTION PROGRAM, AND COMPUTER-READABLE RECORDING MEDIUM AND RECORDING EQUIPMENT

CROSS-REFERENCE TO RELATED APPLICATIONS

The present application claims foreign priority based on Japanese Patent Application No. 2016-036442, filed Feb. 26, 2016, the contents of which is incorporated herein by reference.

BACKGROUND OF THE INVENTION

1. Field of the Invention

The invention relates to an image inspection device, an image inspection method, an image inspection program, and a computer-readable recording medium, or recording equipment.

2. Description of Related Art

There have been utilized image inspection devices that conduct inspection of presence or absence of a surface flaw, an outer appearance shape, reading of printed characters or the like in a workpiece (an inspection object or a subject). The above-described image inspection devices have applied necessary illumination to the workpiece to capture an image, and have performed necessary image processing such as edge detection for obtained image data to determine quality or the like, based on a result.

As one of the above-described image inspection devices, there has been known a device that continuously acquires two-dimensional profile data, which is a two-dimensional cross-sectional shape of a workpiece, to configure data of a three-dimensional shape of the workpiece by moving a two-dimensional profile measuring instrument by an optical cutting method or by an optical scanning method relatively to the workpiece, and creates a distance image (a height image) changing gray values of pixels in accordance with a distance from a camera to the workpiece to inspect quality of the workpiece (e.g., refer to Japanese Unexamined Patent Application Publication No. 2015-31540).

In the above-described image inspection device capable of inspecting the image having height information, since the two-dimensional profile measuring instrument is moved relatively to the workpiece, for example, the workpiece is conveyed by utilizing a conveyance device such as a belt conveyer and a roller conveyer. In this case, there is a problem that if vibration exists in the conveyance device conveying the workpiece, an error is caused in the measurement data in a height direction of a displacement meter.

Thus, in a case where high-accuracy height dimension inspection is required, labor and time of introducing a mechanism in which vibration is prevented from occurring in a conveyance system as much as possible, or preparing a station for measurement has been prepared separately and replacing the workpiece onto the station become necessary, which is a barrier to introduction of the three-dimensional inspection device.

SUMMARY OF THE INVENTION

The invention is achieved in light of the above-described circumstances, and an object of the invention is to provide an image inspection device, an image inspection method, an image inspection program, and a computer-readable recording medium or recording equipment, which enable high-accuracy outer appearance inspection in a height direction by correcting vibration even if the vibration exists.

According to one embodiment of the invention, an image inspection device is an image inspection device for conducting outer appearance inspection, based on height information of an inspection object, the image inspection device including an irradiation part configured to apply measurement light to the inspection object relatively moved in one direction, a detection part configured to detect reflected light that is applied from the irradiation part to the inspection object and is reflected at the inspection object, the reflected light including a vibration component in a height direction, a two-dimensional profile generation part configured to generate a two-dimensional profile indicating a cross-sectional shape of the inspection object, based on detection data obtained by the detection part, a reference height setting part configured to set a reference height as a reference of vibration component estimation, based on three-dimensional data before the vibration component obtained from a plurality of the two-dimensional profiles generated by the two-dimensional profile generation part is removed, a vibration estimation part configured to estimate the vibration component in an inspection environment, based on the two-dimensional profile generated by the two-dimensional profile generation part and the reference height set by the reference height setting part, a profile correction part configured to remove, from each of the two-dimensional profiles, the vibration component estimated by the vibration estimation part, a three-dimensional data generation part configured to generate the three-dimensional data of the inspection object from the plurality of two-dimensional profiles from which the vibration component is removed by the profile correction part, and an inspection part configured to conduct the outer appearance inspection of the inspection object, based on the three-dimensional data generated by the three-dimensional data generation part. With the above-described configuration, even in a situation where when the inspection object and the detection part are relatively moved, the vibration in the height direction occurs, the vibration component is removed, using the profile correction part, which can make unnecessary an antivibration mechanism or a clamp mechanism of the inspection object, and enables high-accuracy image inspection even to a movement system having large vibration.

According to another embodiment of the invention, in the image inspection device, the reference height setting part can estimate a planar reference plane as the reference height, based on the three-dimensional data before the vibration component is removed, the three-dimensional data having been generated by the three-dimensional data generation part, and the vibration estimation part can estimate the vibration component of each of the two-dimensional profiles, based on a reference straight line obtained from a cross section of the reference plane estimated by the reference height setting part, and a height on the two-dimensional profile corresponding to the estimated reference straight line. With the above-described configuration, the vibration component is estimated, based on the reference line, which enables the stable estimation of the vibration component.

According to still another embodiment of the invention, in the image inspection device, the reference height setting part can estimate a reference curved plane as the reference height, based on the three-dimensional data before the vibration component is removed, the three-dimensional data having been generated by the three-dimensional data generation part, and the vibration estimation part can estimate the vibration component of each of the two-dimensional profiles, based on a reference curved line obtained from a cross section of the reference curved plane estimated by the reference height setting part, and a height on the two-dimensional profile corresponding to the estimated reference curved line. With above-described configuration, the vibration component is estimated based on the reference curved plane, which enables the stable estimation of the vibration component.

According to still another embodiment of the invention, in the image inspection device, the reference height setting part can automatically set the reference plane, based on the three-dimensional data before the vibration component is removed. The above-described configuration can make unnecessary setting work by a user.

According to still another embodiment of the invention, the image inspection device can further include a height range designation part configured to designate a height difference in the height direction in the two-dimensional profile, as data that the reference height setting part uses for calculation of the reference height, and the reference height setting part can set the reference height in the two-dimensional profile, based on the data within a height range designated by the height range designation part. With the above-described configuration, on the premise that an amplitude of the vibration component is smaller than the height difference of irregularity of an original shape of the inspection object, the height range for distinguishing the height difference of the irregularity of the inspection object and fluctuation by the vibration component is designated, and data large in height difference is ignored or influence by the same is reduced to set the reference height. This can reduce influence on the calculation of the reference height by the presence or absence of the irregularity or the like in the original shape of the inspection object.

Furthermore, according to still another embodiment of the invention, the image inspection device can further include a reference plane designation part configured to designate a three-dimensional data display region to display the three-dimensional data before the vibration component is removed, and a region as the reference plane in the three-dimensional data displayed in the three-dimensional data display region. Since with the above-described configuration, the user can directly designate the region as the reference plane, a most stable portion can be selected with respect to, for example, the inspection object where a plurality of planes exist, and the correction of the vibration can be stably performed.

Furthermore, according to still another embodiment of the invention, the image inspection device can further include a mask region setting part configured to set a mask region that the reference height setting part is prohibited from setting as the reference for calculating the reference plane from the three-dimensional data before the vibration component is removed. With this configuration, the user can set the mask region that is not the reference for the calculation of the reference plane. Flexible setting in accordance with the inspection object is enabled, for example, by removing a region of the inspection object, avoiding an irregular portion or a portion where the irregularity is likely to occur, or the like.

Furthermore, according to still another embodiment of the invention, in the image inspection device, the reference height setting part can set the reference height, based on the three-dimensional data before the vibration component is removed, the vibration estimation part can estimate the vibration component in the height direction from a relationship between the reference straight line and the two-dimensional profile, and the profile correction part can perform the correction.

Furthermore, according to still another embodiment of the invention, in the image inspection device, the reference height setting part can set the reference height based on the three-dimensional data before the vibration component is removed, the vibration estimation part estimates the vibration component in the height direction and the vibration component around a rotation axis in a movement direction of the inspection object from a relationship between the reference straight line and the two-dimensional profile, and the profile correction part performs the correction.

Furthermore, according to still another embodiment of the invention, in the image inspection device, the reference height setting part can dynamically vary the reference height in accordance with update of the three-dimensional data of the inspection object. The above-described configuration enables even the inconstant vibration dynamically varying to be addressed.

Furthermore, according to still another embodiment of the invention, in the image inspection device, a user manually can input the reference height in the reference height setting part.

Furthermore, according to still another embodiment of the invention, in the image inspection device, the reference height setting part can set one reference profile, based on the two-dimensional profiles configuring the three-dimensional data before the vibration component is removed, and the vibration estimation part can estimate the vibration component, based on the reference profile and the height of the two-dimensional profile corresponding to the reference profile. The above-described configuration enables the outer appearance inspection to be properly performed in the case where the shape of the inspection object is not largely changed in the movement direction.

Furthermore, according to still another embodiment of the invention, in the image inspection device, the reference height setting part can smooth the plurality of two-dimensional profiles in a scanning direction of the inspection object to calculate the one reference profile, and the vibration estimation part can estimate the vibration component of the two-dimensional profile, based on the calculated reference profile.

Furthermore, according to still another embodiment of the invention, in the image inspection device, the reference height setting part can calculate the reference profile, based on the plurality of two-dimensional profiles acquired at adjacent positions, and the vibration estimation part can estimate the vibration component of the two-dimensional profile, based on the calculated reference profile.

Furthermore, according to still another embodiment of the invention, in the image inspection device, the reference profile can be a planar portion in an outer shape of the inspection object.

Furthermore, according to still another embodiment of the invention, in the image inspection device, the vibration estimation part can skip over one or more two-dimensional profiles to discretely select the two-dimensional profiles, and can estimate the vibration component with respect to the selected two-dimensional profiles, and can further complement correction data of the obtained vibration component with respect to the two-dimensional profiles between the selected two-dimensional-profiles. The above-described configuration enables acceleration of processing time to be expected.

Furthermore, according to still another embodiment of the invention, in the image inspection device, the vibration estimation part can calculate the vibration component, based on the two-dimensional profile having height data in which a difference from the reference height set by the reference height setting part is within a predetermined range Furthermore, according to still another embodiment of the invention, in the image inspection device, the vibration component in a portion having the height data outside the predetermined range can be complemented, using an estimation result of the vibration component in a periphery of the portion.

Furthermore, according to still another embodiment of the invention, in the image inspection device, filter processing can be performed to the vibration estimation result by the vibration estimation part. The above-described configuration can stabilize the vibration estimation result.

Furthermore, according to still another embodiment of the invention, the image inspection device further includes a correction mode selection part configured to select any of a vertical vibration correction mode in which the vibration estimation part estimates only the vibration component in the height direction as the vibration component, and a rotational vibration correction mode in which the vibration estimation part estimates a rotational vibration component around the movement direction in addition to the vibration component in the height direction. With the above-described configuration, in the case where the correction of the rotational vibration component makes the estimation result unstable, the correction mode is selected not to perform the rotational vibration correction, which realizes the stable outer appearance inspection.

Furthermore, according to still another embodiment of the invention, the image inspection device can further include a display part configured to display the estimation result of the vibration.

Furthermore, according to still another embodiment of the invention, in the image inspection device, the irradiation part can be a light-emitting element, the detection part can be a light receiver, and the detection data can be luminance data.

Furthermore, according to one embodiment of the invention, an image inspection method is an image inspection method for conducting outer appearance inspection, based on height information of an inspection object, the method including the steps of applying measurement light to the inspection object relatively moved in one direction, and detecting reflected light that is reflected at the inspection object, and includes a vibration component in a height direction, generating a two-dimensional profile indicating a cross-sectional shape of the inspection object, based on the detected detection data, setting a reference height as a reference of vibration component estimation, based on the generated two-dimensional data, estimating the vibration component in an inspection environment, based on the generated two-dimensional profile and the set reference height, removing the estimated vibration component from the two-dimensional profile, generating three-dimensional data of the inspection object from a plurality of the two-dimensional profiles from which the vibration component is removed; and conducting the outer appearance inspection of the inspection object, based on the generated three-dimensional data. Thereby, even in a situation where when the inspection object and the detection part of the measurement light are relatively moved, the vibration in the height direction occurs, the vibration component is removed, which can make unnecessary an antivibration mechanism or a clamp mechanism of the inspection object, and enables high-accuracy image inspection even to a movement system having large vibration.

Furthermore, according to one embodiment of the invention, an image inspection program is an image inspection program for conducting outer appearance inspection, based on height information of an inspection object, the image inspection program causing a computer to implement a two-dimensional profile generation function for detecting reflected light that is applied measurement light to the inspection object relatively moved in one direction, is reflected at the inspection object and includes a vibration component in a height direction, and generating a two-dimensional profile indicating a cross-sectional shape of the inspection object, based on the detected detection data, a reference height setting function for setting a reference height as a reference of vibration component estimation, based on the two-dimensional profile generated by the two-dimensional profile generation function, a vibration estimation function for estimating the vibration component in an inspection environment, based on the two-dimensional profile generated by the two-dimensional profile generation function, and the reference height set by the reference height setting function, a profile correction function for removing, from the two-dimensional profile, the vibration component estimated by the vibration estimation function, a three-dimensional data generation function for generating three-dimensional data of the inspection object from a plurality of the two-dimensional profiles from which the vibration component is removed by the profile correction function, and an inspection function for conducting the outer appearance inspection of the inspection object, based on the three-dimensional data generated by the three-dimensional data generation function. Thereby, even in the situation where when the inspection object and the detection part for detecting measurement light are relatively moved, the vibration in the height direction occurs, the vibration component is removed, using the profile correction part, which can make unnecessary an antivibration mechanism or a clamp mechanism of the inspection object, and enables high-accuracy image inspection even to a movement system having large vibration.

Furthermore, according to one embodiment of the invention, a computer-readable recording medium or recording equipment is a computer-readable recording medium or recording equipment on which the above-described program is recorded. The recording medium includes a CD-ROM, a CD-R, a CD-RW and a flexible disk, a magnetic tape, a magnetic disk such as an MO, a DVD-ROM, a DVD-RAM, a DVD-R, a DVD+R, a DVD-RW, a DVD+RW, Blu-ray (registered trademark), an HD, and a DVD(AOD), an optical disk, a magneto-optical disk, a semiconductor memory, and other mediums capable of storing the program. Moreover, the program includes a form of being distributed by download through a network line such as the internet in addition to the form of being stored in the above-described recording medium and distributed. Further, the recording equipment includes general purpose or dedicated equipment mounted in a state where the above-described program can be executed in a form of software, firmware or the like. Furthermore, processing and functions included in the program may be executed by computer-executable program software, or the processing in the respective parts may be implemented by hardware such as a predetermined gate array (an FPGA, an ASIC), or in a form in which program software and a partial hardware module that implements a part of elements of hardware coexist.

BRIEF DESCRIPTION OF THE DRAWINGS

FIG. 4A is a perspective view showing a state where a workpiece is scanned by a head part, FIG. 4B is a plan view of the workpiece showing scanning positions, and FIG. 4C is a schematic view showing how two-dimensional profiles obtained at the respective scanning positions in FIG. 4B are composed to generate three-dimensional data;

FIG. 17A is a view showing three-dimensional data of a workpiece including the vibration component, FIG. 17B is a view showing a state where data within a height range is extracted from FIG. 17A, FIG. 17C is a view showing a state where a reference plane is extracted from FIG. 17B, FIG. 17D is a view showing how the vibration component is estimated, based on the two-dimensional profile in one cross section in FIG. 17A and a reference straight line corresponding to the reference plane in FIG. 17C, FIG. 17E is a view showing a state where the vibration component is extracted from FIG. 17D, FIG. 17F is a view showing a state where the vibration component in FIG. 17E is acquired for each of the two-dimensional profiles, and FIG. 17G is a view showing three-dimensional data in which the vibration component in FIG. 17F is removed;

DETAILED DESCRIPTION OF PREFERRED EMBODIMENTS

Figure 1:
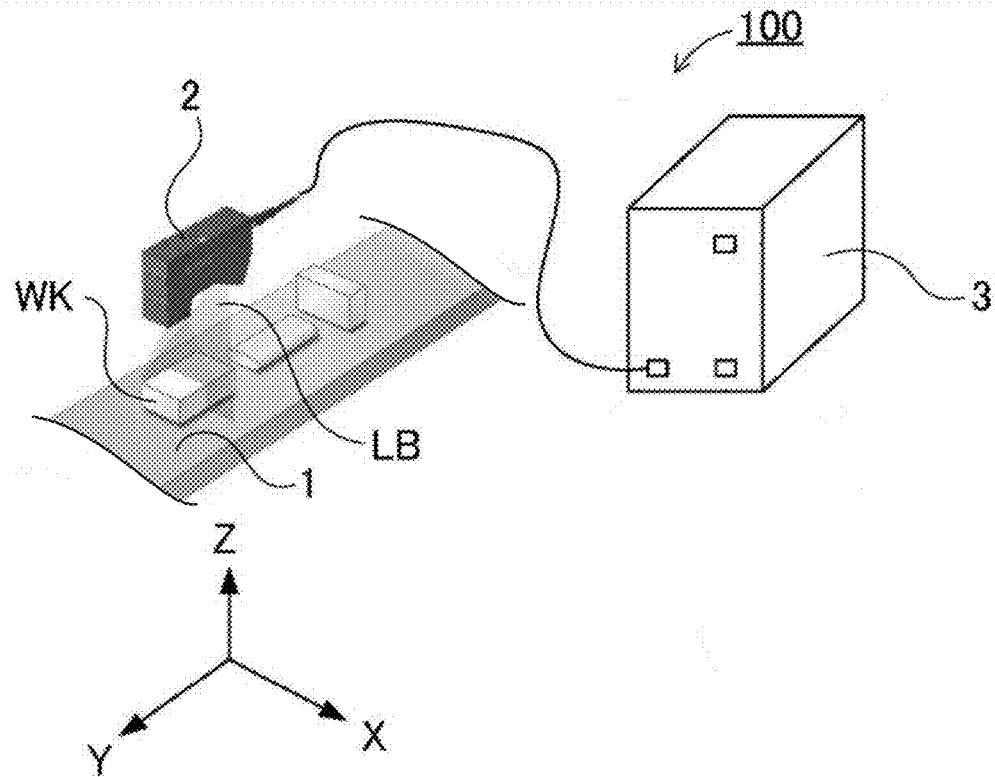
FIG. 1 is a perspective view showing an outer appearance of an image inspection device according to a first embodiment of the invention.

Hereinafter, embodiments of the invention will be described with reference to the drawings. However, the embodiments described below are illustrations for embodying technical ideas of the invention, and the invention is not specified by the following. Moreover, the specification does not specify members described in the scope of the claims to members of the embodiments. Especially, unless specific descriptions are given, dimensions, materials, shapes, relative dispositions and the like of components described in the embodiments are not intended to limit the scope of the invention thereto, but are only explanatory examples. Sizes, positional relations and the like of the members shown in the respective drawings may be emphasized for clarification of description. In the following description, the same names and reference numerals denote the same or equivalent members, and detailed description is omitted as needed. Furthermore, as to respective elements constituting the invention, an aspect may be employed in which a plurality of elements are configured by a same member, and the one member is used for the plurality of elements, or a function of one member can be shared and realized by a plurality of members.

First Embodiment

Figure 2:
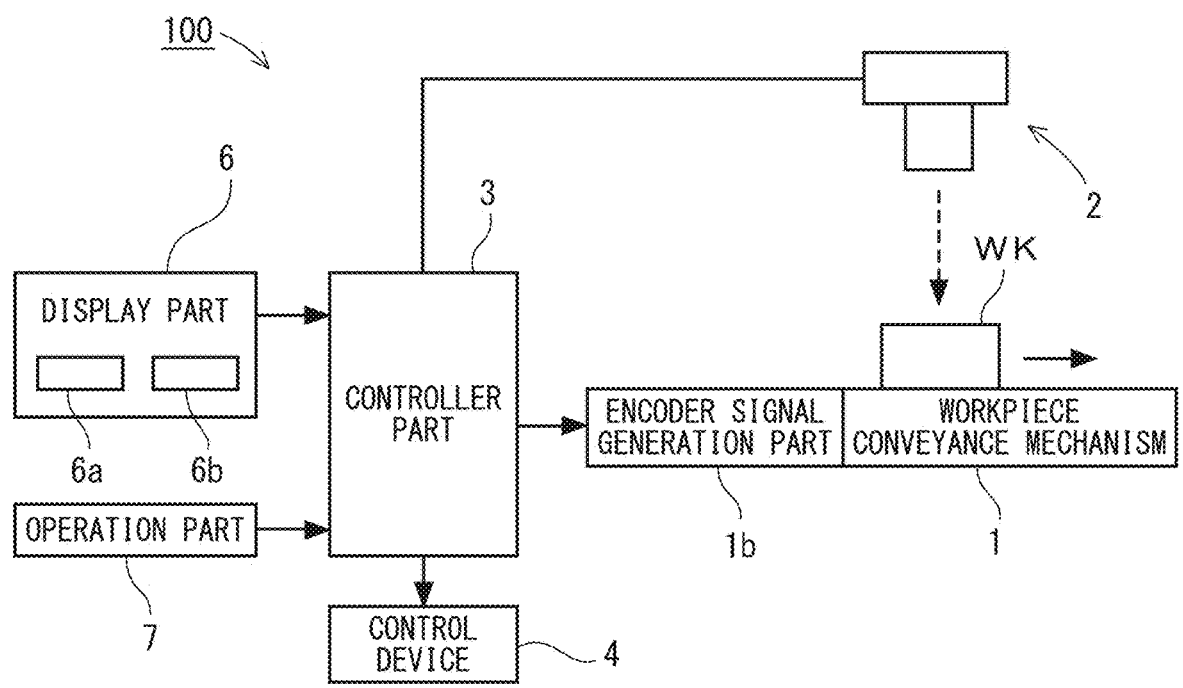
FIG. 2 is a block diagram showing the image inspection device in FIG. 1.
Figure 3:
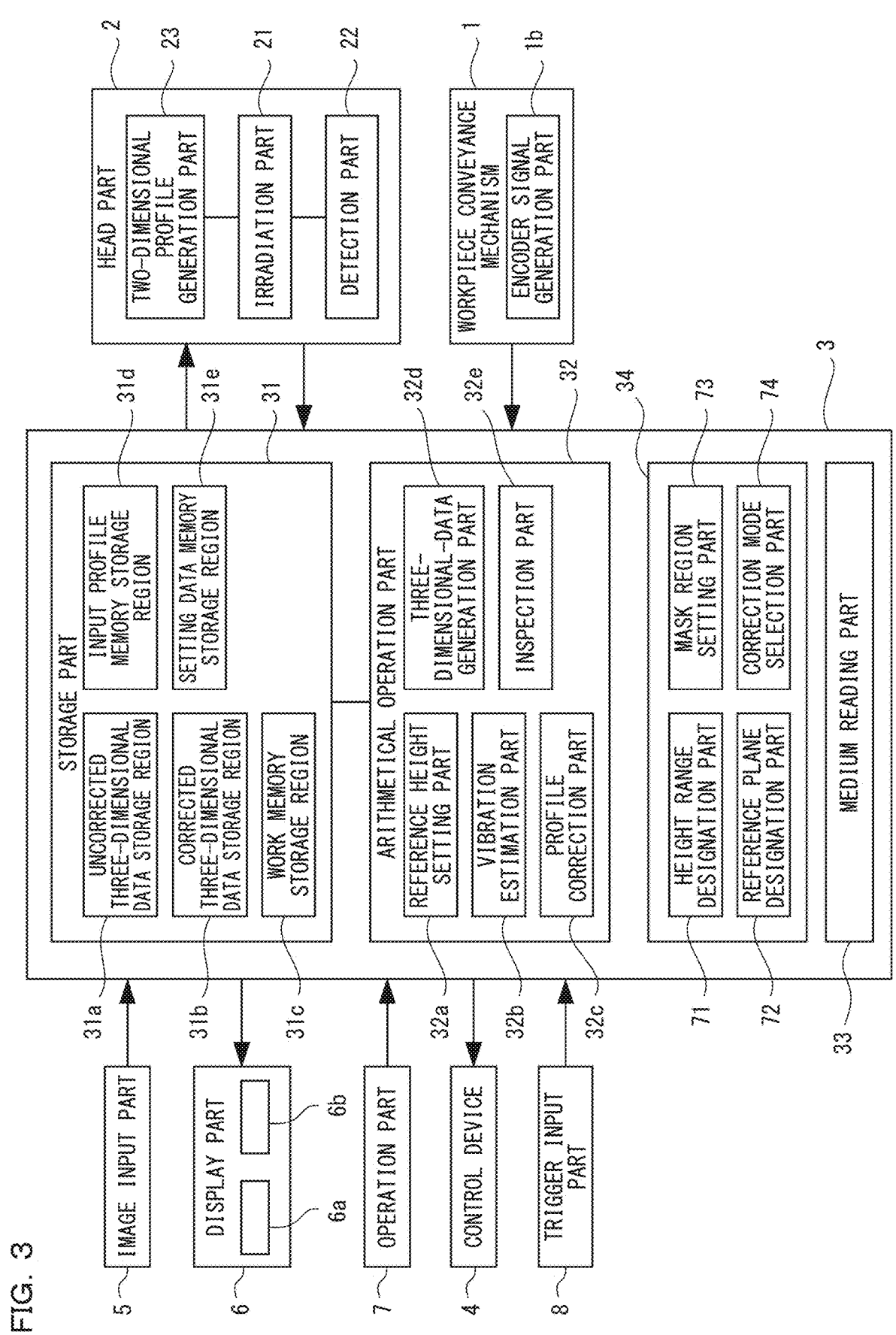
FIG. 3 is a detailed functional block diagram of the image inspection device in FIG. 2.

An outer appearance of an image inspection device according to a first embodiment of the invention is shown in FIG. 1, a block diagram is shown in FIG. 2, and a more detailed functional block diagram is shown in FIG. 3. The image inspection device 100 shown in these diagrams inspects, by image processing, the outer appearance of an inspection object (a workpiece WK) conveyed on a workpiece conveyance mechanism 1. This image inspection device 100 includes a head part 2 that captures an image of the workpiece WK, and a controller part 3 that applies the image processing to the image obtained by the head part 2. The controller part 3 conducts the outer appearance inspection to the image having height information by the image processing to output an inspection result. The outer appearance inspection is a production inspection executed, using the image processing result of the workpiece WK, and includes a dimension inspection for measuring dimensions of the workpiece WK, a non-defective product inspection for determining whether or not the workpiece WK is a non-defective product, and the like. The workpiece conveyance mechanism 1 is a line such as a conveyer controlled by a control device 4 such as a programmable logic controller (PLC).

The image inspection device 100 includes the head part 2 and the controller part 3, as shown in the block diagram of FIG. 3. To the controller part 3 are connected an image input part 5 to input an optical image separately, a display part 6, an operation part 7, the control device 4, and a trigger input part 8. Moreover, a signal from an encoder signal generation part 1b of the workpiece conveyance mechanism 1 is inputted to the controller part 3, so that it can be grasped that the workpiece WK is being conveyed by the workpiece conveyance mechanism 1, or that the conveyance of the workpiece WK is stopped. The encoder signal generation part 1b is, for example, a rotary encoder provided at a rotating shaft of a conveyer for the signal indicating an operation state of the workpiece conveyance mechanism 1. The image input part 5 is a unit with a connector. The image input part 5 is not limited to an aspect in which the image input part is externally attached, but an aspect in which the image input part is built in the controller part 3 may be employed.

The trigger input part 8 is a member to indicate imaging timing of the workpiece WK to the controller part 3. For example, a trigger signal from a photoelectronic sensor disposed on the workpiece conveyance mechanism 1 is received by the trigger input part 8, by which it is detected that the workpiece WK has been conveyed, so that timing when processing such as the imaging, and the outer appearance inspection is performed can be set.

(Operation Part 7)

The operation part 7 is a member to perform various operations and settings to the controller part 3. A keyboard, a console, a pointing device such as a mouse can be utilized.

(Display Part 6)

The display part 6 is a member to display an obtained two-dimensional profile or height image, an estimation result of vibration, and a result of the outer appearance inspection, a setting screen for making various settings, setting values inputted to this setting screen from the operation part 7, and so on. The above-described display part 6 is a display of an LCD, a CRT, an organic EL or the like. Moreover, in the case where the display part 6 is made of a touch panel, it can function as both the operation part and the display part. Moreover, this display part 6 has a two-dimensional profile display region 6a to display the two-dimensional profile, and a three-dimensional data display region 6b to display three-dimensional data.

(Head Part 2)

The head part 2 is a member to measure the two-dimensional profile of the workpiece WK. As shown in the block diagram of FIG. 3, the head part 2 includes an irradiation part 21 to apply measurement light to the workpiece WK relatively moved in one direction, a detection part 22 to detect reflected light that is applied to the workpiece WK from the irradiation part 21 and is reflected, including a vibration component in a height direction, and a two-dimensional profile generation part 23 to generate the two-dimensional profile showing a cross-sectional shape of the workpiece WK, based on detection data acquired by the detection part 22. In the specification, the "height direction" is used as a distance direction between the head part 2 (exactly, the detection part 22) and the workpiece WK.

In this head part 2, as shown in FIG. 4A, the irradiation part 21 applies a wide laser beam LB in an X-axis direction (a width direction) to the workpiece WK conveyed in a Y-axis direction (a feeding direction) and receives reflected light by the detection part 22, so that the two-dimensional profile generation part 23 creates the two-dimensional profile as data indicating a two-dimensional cross-sectional shape of the workpiece WK. At this time, the workpiece WK is virtually cut along a cut surface parallel to an XZ plane, and an outer shape (an outer edge) of the cut surface serves as the two-dimensional profile (FIGS. 4B and 4C). The two-dimensional profile is generally a set of distances from the head part 2 to measurement points of the workpiece WK (distances in a Z-axis direction), that is, a set of distances of the plurality of measurement points lined along the X-axis direction.

For the head part 2, a laser displacement meter of a line projection type is used. Specifically, the head part 2 includes a light projecting element that emits the laser beam LB or the like as the irradiation part 21, and a light receiving element (a line sensor or a two-dimensional imaging element) such as a CCD as the detection part 22. Furthermore, the head part 2 includes an optical system such as lenses to guide the applied light and the reflected light. This head part 2 can also be considered as a camera to image the workpiece WK.

In the specification, an example will be described, in which using the head part 2 by an optical cutting method shown in FIG. 1, a height image obtained by composing a two-dimensional profile images obtained by the optical cutting method is used. However, the invention is not limited to this method as the method for acquiring the height image, but any well-known method that enables height information to be acquired can be employed as needed. Examples of a method using a principle of triangulation include a stripe projection image method, a phase shift method, a space coding method, a random pattern projection method, and the like. Moreover, examples of non-contact active three-dimensional measurement methods using other than the principle of triangulation include a Time of Flight (TOF) method, a confocal method or the like. Alternatively, an example of a non-contact passive three-dimensional measuring method includes a focal method such as a stereo method (a stereo method after calibration or photogrammetry), a lens focal method and the like. A configuration of the head part is set as needed in accordance with these methods for acquiring the height information of the workpiece.

While in the specification, the laser displacement meter is employed to obtain the height image, another method such as a TOF method may be used. In the specification, examples of the measurement light and the reflected light that can be used include visible light, infrared light, ultraviolet light or the like.

While in the example of FIG. 1, a configuration is employed in which the head part 2 and the controller part 3 are physically separated, the invention is not limited to this configuration, and for example, a configuration can also be employed in which the head part 2 and the controller part 3 can be integrated. While in configuration of FIG. 1, the irradiation part 21 and the detection part 22 are incorporated in the common head part 2, the invention is not limited to this configuration, but the configuration may be such that the irradiation part and the detection part are separately disposed. Alternately, the two-dimensional profile generation part may be disposed on the controller part side, or on the contrary, the three-dimensional data generation part may be provided on the head part side. Moreover, in FIG. 1, the head part 2 is connected to a connector for the head of the controller part 3 through a cable. However, the connection is not limited to wired connection, but wireless connection is also enabled. Moreover, network connection through a communication protocol may be employed.

(Controller Part 3)

The controller part 3 shown in FIG. 3 includes a storage part 31, an arithmetical operation part 32, a medium reading part 33, and a setting part 34. The arithmetical operation part 32 includes a reference height setting part 32a, a vibration estimation part 32b, a profile correction part 32c, a three-dimensional data generation part 32d, and an inspection part 32e. The storage part 31 is a member to store various types of image data and setting data, and includes an uncorrected three-dimensional data storage region 31a, and a corrected three-dimensional data storage region 31b, a workpiece memory storage region 31c, an input profile memory storage region 31d, a setting data memory storage region 31e and the like. The medium reading part 33 is a member to read a portable medium or write in the portable medium, and a recording medium, a semiconductor memory or the like, which are standardized, such as a USB memory (product name), and an SD card (product name) is connected to enable the reading and writing of the data. Moreover, the configuration may be such that the data is received and transmitted with respect to external recording equipment through wireless connection or network connection.

The reference height setting part 32a is a member to set a reference height, which is a reference of vibration component estimation, based on the two-dimensional profile generated by the two-dimensional profile generation part 23. The reference height setting part 32a utilizes the two-dimensional profile and the three-dimensional data obtained by composing the two-dimensional profiles to arithmetically operate the reference height. For example, a planar portion can be extracted from the three-dimensional data of the workpiece to utilize the planar portion as the reference height (a reference plane). Moreover, the reference height is not limited to a surface, but for example, a linear portion can also be extracted from the two-dimensional profile indicating a cross-sectional shape at a specific position of the workpiece in the Y direction to utilize the same as the reference height (a reference line), or a plurality of specific points are extracted to utilize the same as the reference height (reference points).

The vibration estimation part 32b is a member to estimate the vibration component in an inspection environment, based on the two-dimensional profile generated by the two-dimensional profile generation part 23, and the reference height set by the reference height setting part 32a. The profile correction part 32c is a member to remove the vibration component estimated in the vibration estimation part 32b from each of the two-dimensional profiles. The three-dimensional data generation part 32d is a member to generate the three-dimensional data of the inspection object from the plurality of two-dimensional profiles from which the vibration component is removed by the profile correction part 32c. The inspection part 32e is a member to conduct the outer appearance inspection of the inspection object, based on the three-dimensional data generated by the three-dimensional data generation part 32d.

The setting part 34 includes a height range designation part 71, a reference plane designation part 72, a mask region setting part 73, and a correction mode selection part 74. The height range designation part 71 is a member to designate a height difference in the height direction in the two-dimensional profile as data that the reference height setting part 32a uses for calculation of the reference height. The reference plane designation part 72 is a member to designate a region as a reference plane in the three-dimensional data displayed in the three-dimensional data display region. The mask region setting part 73 is a member to set a mask region that is prohibited from being set as a reference for calculating the reference plane from the three-dimensional data before the vibration component is removed. The correction mode selection part 74 is a member to select one of a vertical vibration correction mode in which the vibration estimation part 32b estimates the vibration component in the height direction as the vibration component, and a rotational vibration correction mode in which the vibration estimation part 32b estimates a rotational vibration component around a movement direction in addition to the vibration component in the height direction.

The arithmetical operation part 32 can be implemented, for example, by a microprocessor (an MPU), a CPU, an LSI, a gate array such as an FPGA and an ASIC, hardware and software of a DSP and the like, or by mixing these. Moreover, the respective components need not be the same as those in the configuration shown in FIG. 3, and a component having substantially the same function and a component having the functions of the plurality of elements in the configuration shown in FIG. 3 are included in the invention.

(Vibration Correction Function)

Figure 9:
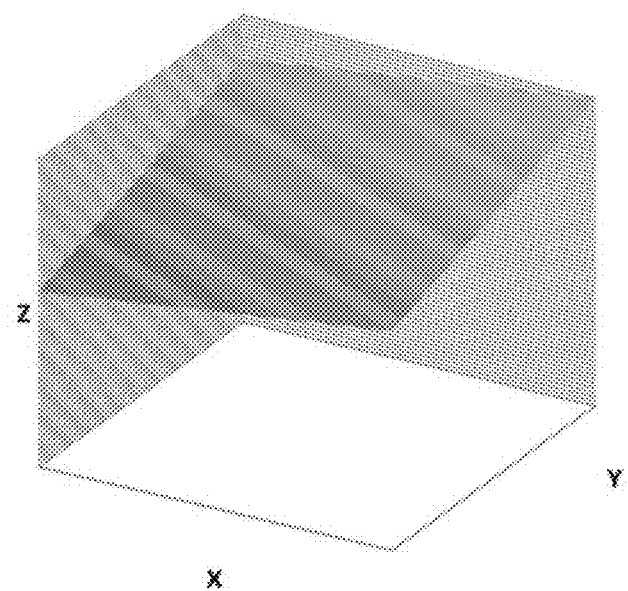
FIG. 9 is an image view showing a three-dimensional image obtained by measuring a plane having no vibration.
Figure 10:
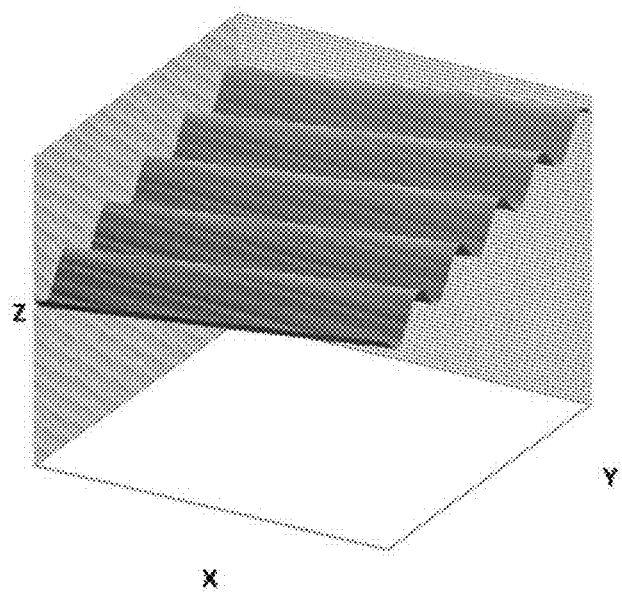
FIG. 10 is an image view showing a three-dimensional image in a state where the vertical vibration component is applied to the plane in FIG. 9.

Using the above-described scanning type image inspection device 100, the outer appearance inspection of the workpiece WK conveyed by the workpiece conveyance mechanism 1 is conducted. This is shown in a side view of FIG. 5. In this case, if vibration occurs when the workpiece WK is conveyed by the workpiece conveyance mechanism 1, an error is caused in the measurement data in the height direction. For example, when a belt conveyer, a roller conveyer, or the like is used as the workpiece conveyance mechanism 1, the workpiece WK goes up and down in the height direction due to irregularity of the conveyer. As one example, if a plane vibrating in the height direction (a vertical direction) is measured with respect to the three-dimensional image obtained by measuring a plane having no vibration as shown in FIG. 9, the plane is detected as a wavy shape as shown in FIG. 10, and a measurement error is caused. In this manner, since in the workpiece conveyance mechanism having relatively large vibration, fluctuation due to the vibration is remarkable, an expensive workpiece conveyance mechanism and scanning device in which the vibration is suppressed need to be introduced to conduct the outer appearance inspection with high accuracy, which is a barrier to the introduction of the image inspection device.

Consequently, in the image inspection device 100 according to the present first embodiment, a precondition that the height can be roughly estimated is given to thereby estimate the vibration component, and the estimated vibration component is subtracted, by which the height data when no vibration exists can be generated. Hereinafter, the description will be given of a case of linear scanning where a direction in which the workpiece WK is moved relatively to the head part 2 is linear, and a case of rotary scanning where the movement direction of the workpiece WK is a rotation direction and the scanning direction rotates relatively around the workpiece WK.

(Linear Scanning)

Figure 5:
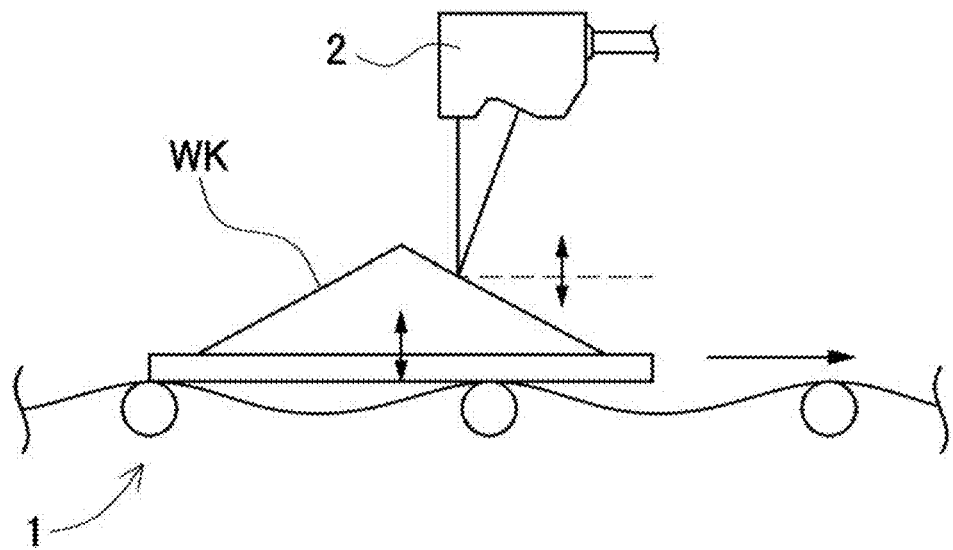
FIG. 5 is a side view showing how vibration occurs when outer appearance inspection of the workpiece conveyed by a workpiece conveyance mechanism.

In the case of the linear scanning, as shown in FIG. 5, if the vibration occurs in the workpiece conveyance mechanism 1, in addition to the proper height component indicated by broken line in the figure, the vibration component is added to a measurement value. This vibration component varies every imaging time. Thus, the two-dimensional profiles imaged at different times have the different vibration components.

(Rotary Scanning)

Figure 6:
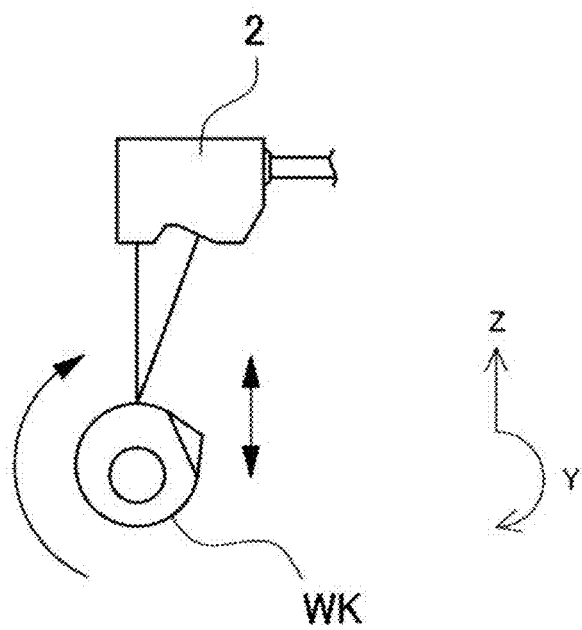
FIG. 6 is a side view showing how vibration occurs in rotary scanning of the workpiece.

On the other hand, an example of the rotary scanning is shown in a cross-sectional view of FIG. 6. Here, a case is considered where the rod-like workpiece WK is rotated around a length direction (an X-axis direction) and a surface of the workpiece WK is measured by the head part 2. Here, a circular arc direction in the rotation is a Y axis and a distance between the workpiece WK and the head part 2 is a Z-axis direction. If a rotation axis of the workpiece WK deviates from a center of a circle, which is a workpiece cross-sectional shape, the workpiece WK fluctuates up and down in the height direction (the Z-axis direction).

If a function to find the height z is modeled from the above-described coordinate position (x, y), it can be represented by the following expression (1).

$$z(x,y) = \text{Height}(x,y) + \text{Error}(x,y) \tag{1}$$

In the above expression, z (x, y) denotes a measurement value of the height, Height (x, y) denotes an actual height, and Error (x, y) denotes an error, in this case, the vibration component.

(Modeling of Vibration)

Figure 7:
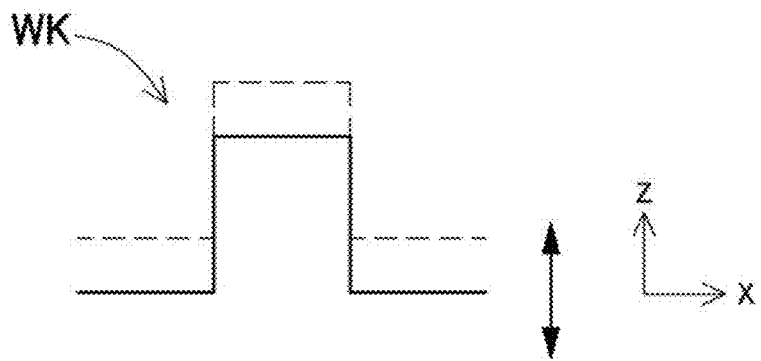
FIG. 7 is a schematic view showing fluctuation of a cross section of the workpiece by a vertical vibration component.
Figure 8:
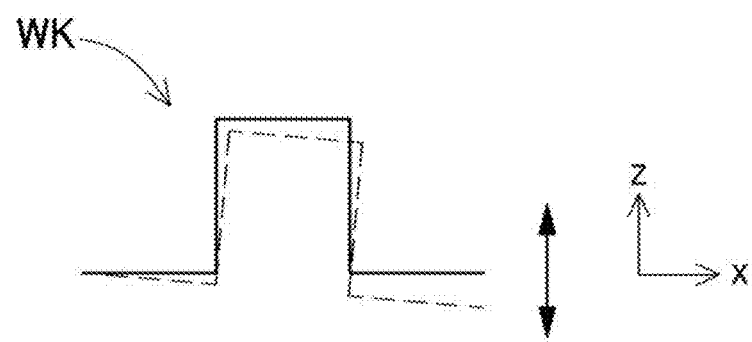
FIG. 8 is a schematic view showing fluctuation of a cross section of the workpiece by a rotational vibration component.

The above-described vibration Error (x, y) is modeled. Here, the workpiece is considered to be a rigid body. Moreover, as to one two-dimensional profile obtained from measuring a cross section of the workpiece, a momentary cross section is measured. Moreover, in modeling of the vibration, attention is paid only to the vibration components in the height direction (the Z-axis direction) and in the conveyance direction (the Y direction) of the workpiece, and vibration other than these vibration components are excluded. The vertical vibration component in the Z-axis direction is fluctuation in the height direction in a cross-section of the workpiece WK, as shown in FIG. 7, and the rotational vibration component around the Y axis is right and left swinging or shaking along the conveyance direction (the Y-axis direction), as shown in FIG. 8. In general vibration, an angle of the rotational vibration component is small, so that it can be considered that a coordinate deviation in the X-axis direction by the rotation is kept to a negligible extent. In this manner, of the vibration components, the component having smaller influence on the measurement in the height direction is excluded for modeling, which can simplify processing of the vibration correction and can make mounting and introduction easy. As a result, the modeled vibration components can be represented by the following expression (2).

$$\text{Error}(x,y) = \text{Offset}(y) + \text{Rot Tan}(y)^* x \tag{2}$$

In the above expression, Error (x, y) is an error (the vibration component), Offset (y) is the vibration component in the Z direction, and Rot Tan (y) is the rotational vibration component (a tangent) around the Y axis.

(Simulation of Vibration Model)

Figure 11:
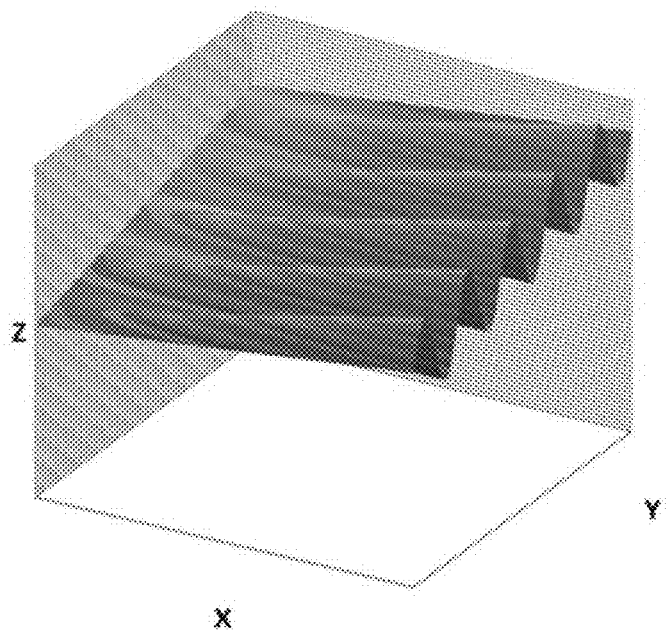
FIG. 11 is an image view showing a three-dimensional image in a state where a rotational vibration component is applied to the plane in FIG. 9.
Figure 12:
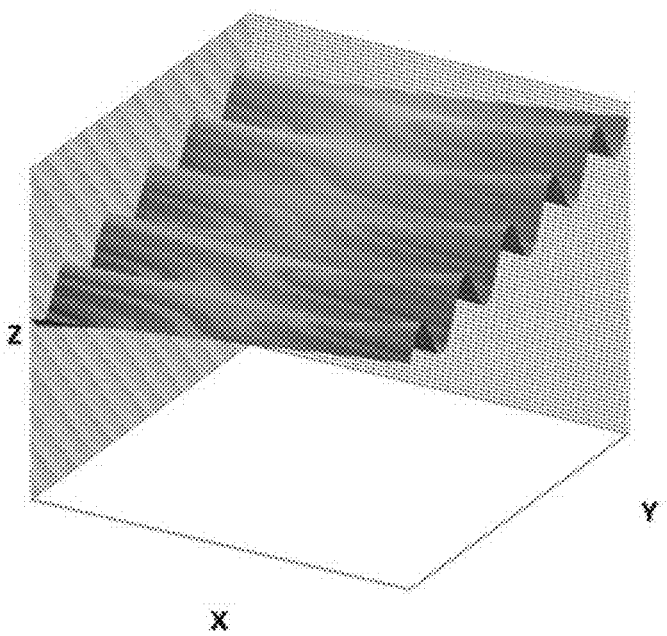
FIG. 12 is an image view showing a three-dimensional image in a state where the vertical vibration component and the rotational vibration component are applied to the plane in FIG. 9.

Simulation results when the plane receives the vibration, based on the modeling of the vibration according to the above-described first embodiment are shown in FIGS. 9 to 12 by being divided into four patterns, based on presence and absence of the vertical vibration and presence or absence of the rotational vibration. In these views, FIGS. 9, 10 show patterns with no rotational vibration, and FIGS. 11 and 12 show patterns with the rotational vibration. Moreover, FIGS. 9 and 11 show the patterns with no vertical vibration, and FIGS. 10 and 12 show the patterns with the vertical vibration. In each of the views, the simulation is performed with a sine wave having a fixed frequency. It can be considered that the real vibration is slightly irregular. The presence or absence of the vertical vibration component and the rotational vibration component causes irregularity in the three-dimensional shape, which should originally be a plane, and this affects accuracy of the height measurement. Therefore, the vibration correction is performed, using the vibration correction part.

(Vibration Correction)

The above-described expressions (1) and (2) for the modeling of the vibration are deformed to obtain the following expression (3).

$$\text{Height}(x,y) = z(x,y) - \text{Offset}(y) - \text{Rot Tan}(y) * x \quad (3)$$

In the above expression, Height (x, y) denotes the actual height, z (x, y) denotes the measured value of the height, Offset (y) denotes the vibration component in the Z direction, and Rot Tan. (y) denotes the rotational vibration component (the tangent) around the Y axis.

In the above expression, estimating the vibration component that is a function of y enables bad influence by the vibration component to be removed from the measured height value.

(Vibration Estimation)

As described above, since the vibration component is the function of y, the vibration component only needs to be found in each of the two-dimensional profiles. As methods for finding the vibration component, the following two methods can be mainly considered.

1. A method of using a plane existing in the inspection object (plane correction)
2. A method of estimating an object two-dimensional profile from previous and subsequent two-dimensional profiles (equal cross section correction)

The former plane correction is suitable for a case where a plane exists in the workpiece. Especially, since in many industrial products, a plane exists, this method can be utilized in many cases of the industrial products. Alternately, a plane in a background such as the belt conveyer on which the workpiece is placed can also be utilized. On the other hand, the latter equal cross section correction is suitable for a case where a cross section of the workpiece does not largely vary. It is preferable for a case where, for example, a cross section of a cable is inspected.

(1. Vibration Estimation: Plane Correction)

Figure 13A:
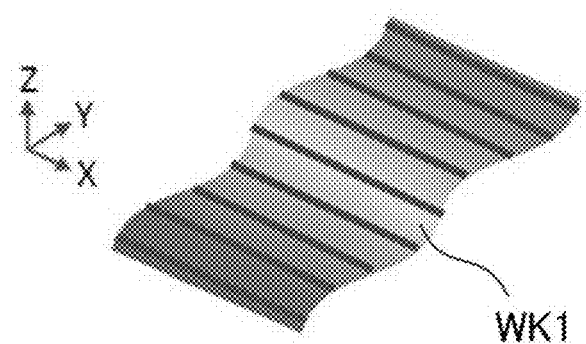
FIG. 13A is an image view showing an input height image of an inspection object.
Figure 13B:
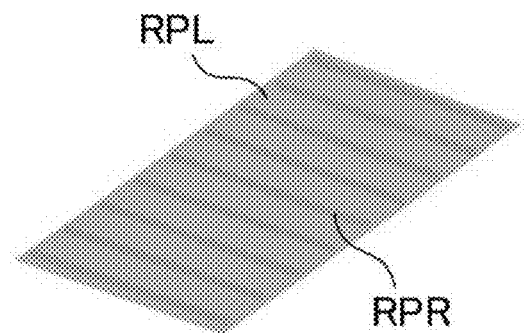
FIG. 13B is an image view showing a reference plane calculated form FIG. 13A.

The plane correction is a method in which the plane existing in the workpiece is utilized as the reference height (the reference plane) to perform the correction. The plane correction is performed, for example, by the reference height setting part 32a. The reference height setting part 32a extracts a planar portion of the workpiece by the image processing from a solid shape of the three-dimensional data obtained by composing the two-dimensional profiles. This is shown in FIGS. 13A to 13B. In these views, FIG. 13A shows a shape of an inspection object WK1 having vibration, and an input height image (an input profile) of the conveyer belt having the vibration, the workpiece disposed on the conveyer belt or the like is shown. FIG. 13B shows a reference plane RPL calculated from FIG. 13A. First, as shown in FIG. 13A, the reference height setting part 32a acquires the two-dimensional profiles at predetermined intervals along the Y-axis direction, which is the conveyance direction of the workpieces. The obtained two-dimensional profiles are composed by the three-dimensional data generation part 32d to thereby obtain the height image as the three-dimensional data.

Next, the reference height setting part 32a arithmetically operates the reference plane RPL from this height image, as shown in FIG. 13B. For a method for extracting the reference plane RPL from the three-dimensional height image, a well-known method or algorism can be utilized. For example, RANSAC (RANDdom SAmple Consensus), a least squares method with outlier elimination or the like can be utilized.

A position of the reference plane RPL is detected at each imaging position of the two-dimensional profiles along the Y-axis direction, based on the reference plane RPL obtained in this manner. Here, a reference straight line RPR, which is a profile on the reference plane RPL where the reference plane RPL and the two-dimensional profile cross each other, is calculated. The vibration estimation part 32b estimates the vibration component from a difference between the reference straight line RPR on the reference plane RPL and the two-dimensional profile. The estimation of the vibration component is performed for each of the two-dimensional profiles. The profile correction part 32c removes the estimated vibration component from each of the two-dimensional profiles, and the three-dimensional data is reconstructed, using the two-dimensional profiles after the vibration component is removed. This brings about the height image with the vibration component removed from the estimated value.

(2. Vibration Estimation: Equal Cross Section Correction)

Figure 14A:
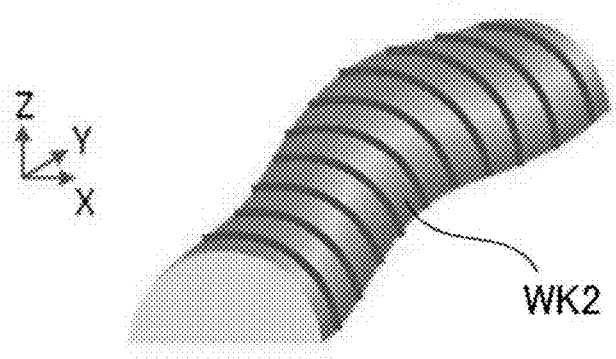
FIG. 14A is an image view showing an input height image of a workpiece.

On the other hand, the equal cross section correction is a method of estimating the two-dimensional profile of the workpiece from the adjacent two-dimensional profiles. This will be described with reference to FIGS. 14A to 14B. In these views, FIG. 14A shows an input height image (an input profile) of a workpiece WK2 vibrating in the height direction as in FIG. 13A, which is three-dimensional data obtained by imaging the workpiece WK2 having almost equal cross sections such as a cable. This input height image is also obtained by composing the two-dimensional profiles acquired at predetermined intervals along the Y-axis direction as the conveyance direction of the workpiece in the three-dimensional data generation part 32d, as in the above-described FIG. 13A.

Figure 14B:
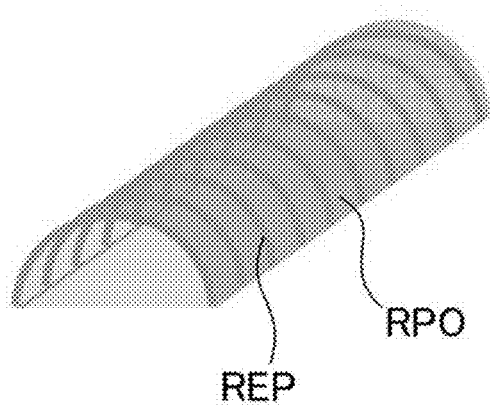
FIG. 14B is an image view showing a reference curved lines calculated form FIG. 14A.

A reference curved plane RRO as shown in FIG. 14B is extracted from this input height image by the reference height setting part 32a. Based on the obtained reference curved plane RRO, a reference curved line REP where a reference curved plane RRO equal cross section and the two-dimensional profile cross each other is calculated at each imaging position of the two-dimensional profiles along the Y-axis direction. The vibration estimation part 32b estimates the vibration component from a difference between the reference curved line REP and the input profile. The profile correction part 32c removes the estimated vibration component to reflect the same on the height image. This brings about the height image with the vibration component removed from the measured value.

(Processing Flow of Vibration Correction Function)

Figure 15:
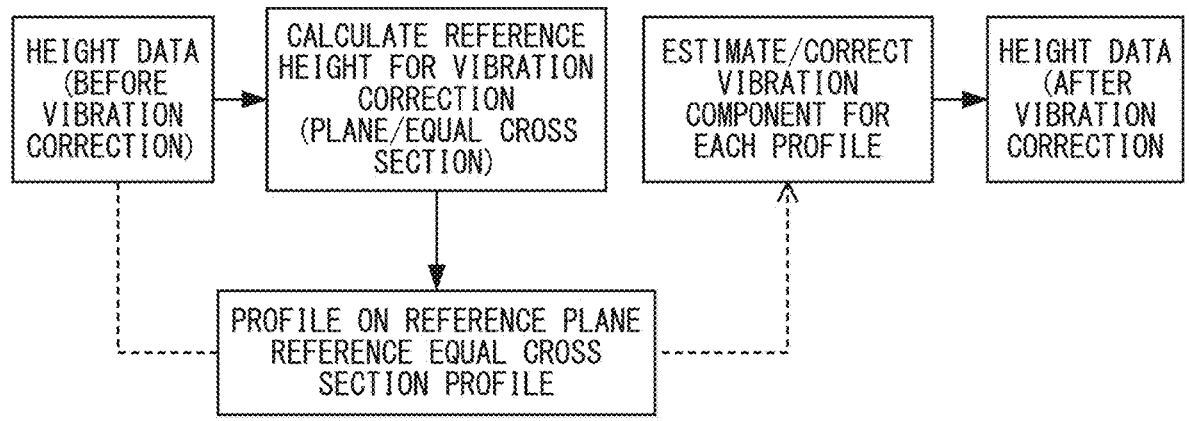
FIG. 15 is a flow chart showing a processing flow of vibration correction function.

Next, a flow of processing of the data when the vibration correction function is applied to the height data obtained by imaging the workpiece, using the above-described vibration correction function is shown in a processing flow in FIG. 15. As shown in this diagram, the reference height for vibration correction (e.g., the reference plane, the reference equal cross section, the reference curved plane) is calculated by the reference height setting part 32a from the height data before the vibration correction, which has been obtained by the head part. The reference straight line RPR or the reference curved line REP on the obtained reference plane RPL is compared with the original height data before the vibration correction to estimate and correct the vibration component for each of the profiles, and the two-dimensional profiles after the vibration correction are composed, by which the height data after the vibration correction can be obtained.

In this manner, the vibration component can be removed from the obtained three-dimensional data. The vibration component to be removed is corrected in the height direction (the Z-axis direction) in the above-described plane correction or equal cross section correction. However, the vibration correction is not limited thereto, and may be applied in the rotation direction (an Rx-axis direction) in addition to or in place of the height direction.

(Height Range Designation Part 71)

Figure 16A:
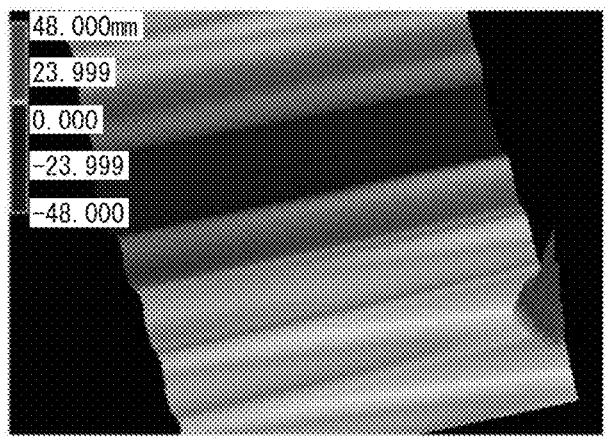
FIG. 16A is and image view showing a height image before vibration component removal.
Figure 16B:
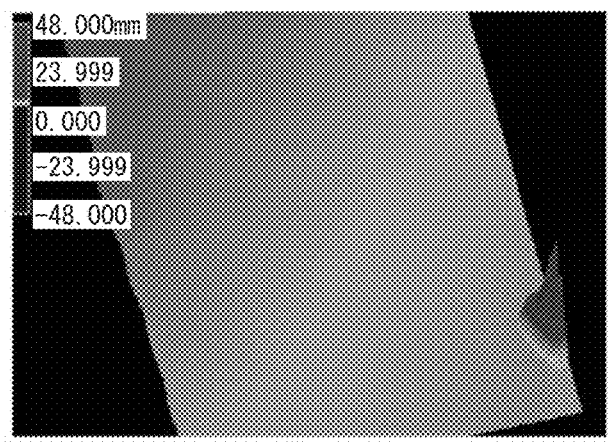
FIG. 16B is an image view showing the height image after the vibration component removal.

Here, in removing the vibration component, an irregular shape that the workpiece originally has needs to be prevented from being impaired. A height range D, which is regarded as vibration, is prescribed, and a height difference outside this range is not treated as the vibration and is excluded from an object of the vibration correction, by which impairment of the original shape of the workpiece is avoided. The setting of the height range D is performed by the height range designation part 71 in FIG. 3. A user designates the height range D with the height range designation part 71 so as to keep an amplitude of the vibration within the height range D. This can effectively remove the vibration having an amplitude smaller than the height difference in the irregularity of the workpiece. For example, as shown in FIG. 16A, with respect to a height image of a workpiece having vibration (vibration correction function OFF), the vibration correction function is turned ON, which can remove only wavy irregularity attributed to the vibration component, and maintain a projection (lower right in the figure) that the workpiece originally has, as shown in FIG. 16B. As the height range D, beside the designation by the user, a default value may be beforehand set on the three-dimensional image inspection device. The height range D may be set to, for example, 0.01 mm to 2 mm or 0.05 mm to 1 mm, 0.1 mm or the like in accordance with a situation or a purpose of the inspection object.

(Procedure for Removing Vibration Component from Three-Dimensional Data)

Here, a procedure for removing the vibration component from the three-dimensional data will be described in detail with reference to FIGS. 17A to 17G. First, the three-dimensional data of a workpiece WK3 including the vibration component as shown in FIG. 17A is generated by the three-dimensional data generation part 32d in FIG. 3. This workpiece WK3 is provided with a semicylindrical projection at a central portion. Next, data included in the height range D set by the height range designation part 71 is extracted from this three-dimensional data. As a result, as shown in FIG. 17B, three-dimensional data from which the projected shape provided at center of the workpiece WK3 is excluded can be obtained. In this manner, points outside the height range D are excluded from a basis of the calculation of the reference plane, by which the reference plane can be precisely calculated without affecting the irregular shape of a surface of the workpiece.

Furthermore, with respect to this three-dimensional data, the reference height setting part 32a performs the estimation of the reference plane. As a result, the reference plane as shown in FIG. 17C can be obtained. As shown in this view, the reference plane is set not only in the range from which the data has been extracted but as a whole.

Next, the estimation of the vibration component is performed for each of the two-dimensional profiles. Here, from the three-dimensional data in FIG. 17A, the reference straight line RPR at a corresponding position on the reference plane (a position indicated by thick line in FIG. 17C) is extracted at each of the positions where the two-dimensional profiles are generated (a position indicated by thick line in FIG. 17A). Then as shown in FIG. 17D, of points configuring the two-dimensional profile, points close to the reference straight line RPR are used to estimate the vibration component. Here, points of the two-dimensional profile included in a range apart by a predetermined distance d from the reference straight line RPR are extracted by the vibration estimation part 32b to arithmetically operate profile points WPP of the workpiece WK3 (indicated by thin line in FIG. 17D).

A difference between the profile points WPP obtained in the above-described manner and the reference straight line RPR is arithmetically operated by the vibration estimation part 32b as a vibration component VIB. As a result, as shown in FIG. 17E, the vibration component in one cross section in the three-dimensional data is arithmetically operated. As shown in FIG. 17F, similar arithmetical operation is performed for each of the two-dimensional profiles, and finally, the vibration component of each of the two-dimensional profiles is subtracted from the three-dimensional data including the vibration component in FIG. 17A on a basis of the two-dimensional profile to reconstruct the three-dimensional data. This can bring about the three-dimensional data after the vibration correction with the vibration component removed, e.g., the height image, as shown in FIG. 17G.

In this manner, in the calculation of the reference plane, the two-dimensional plane is fitted to the plane region of the workpiece WK3 within the height range D, and on the other hand, in the calculation of the profile points WPP of the workpiece WK3, the profile points WPP indicating a planar portion of the workpiece WK3 within the predetermine distance d from the reference straight line RPR indicating the reference plane are fitted one-dimensionally. Here, the height range D and the predetermined distance d can also be set to the same value. This can simplify the fitting processing. However, the height range D of the fitting of the two-dimensional reference plane and the predetermined distance d of the one-dimensional profile points WPP can also be set to be different values.

Figure 18A:
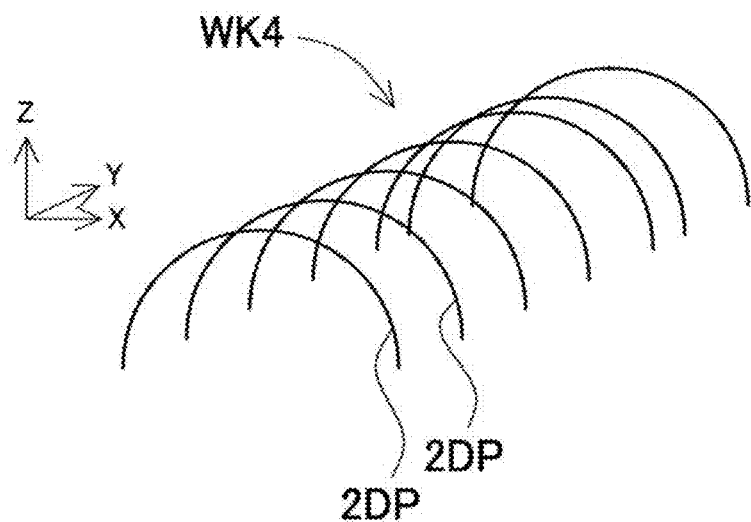
FIG. 18A is a schematic view showing a plurality of two-dimensional profiles of a workpiece.
Figure 18B:
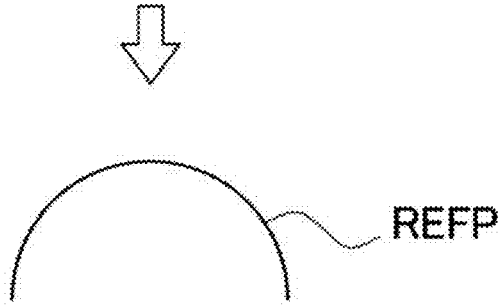
FIG. 18B is a schematic view showing a reference profile obtained from FIG. 18A.
Figure 19:
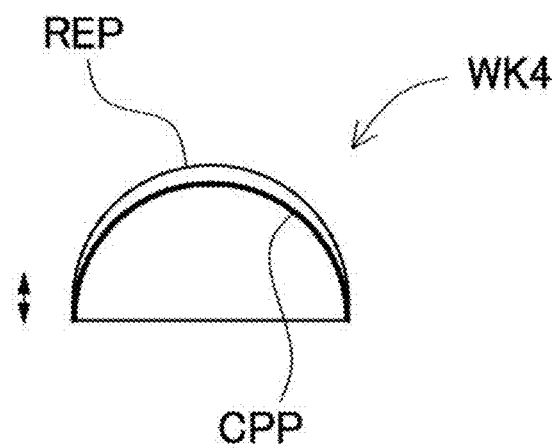
FIG. 19 is a cross-sectional view showing how equal cross section correction is performed to the two-dimensional profile of the workpiece.

On the other hand, in the equal cross section correction as well, an averaging filter in the conveyance direction (the Y-axis direction) of a workpiece WK4 having almost equal semi-circular cross sections continued as shown in FIG. 18A is applied to two-dimensional profiles 2DP of the workpiece WK4 to create a reference profile REFP shown in FIG. 18B. In other words, the reference profile REFP is obtained by averaging the two-dimensional profiles 2DP adjacent in the Y-axis direction. A size of the averaging filter used here is made larger than a magnitude of the vibration. The reference profile REFP obtained in this manner is used as the reference curved line REP and points of the two-dimensional profile 2DP close in distance are extracted by the vibration estimation part 32b, and as shown in FIG. 19, the vibration component is estimated by the vibration estimation part 32b from a difference between the extracted measured points CPP on the cross section, and the reference curved line REP.

Figure 20:
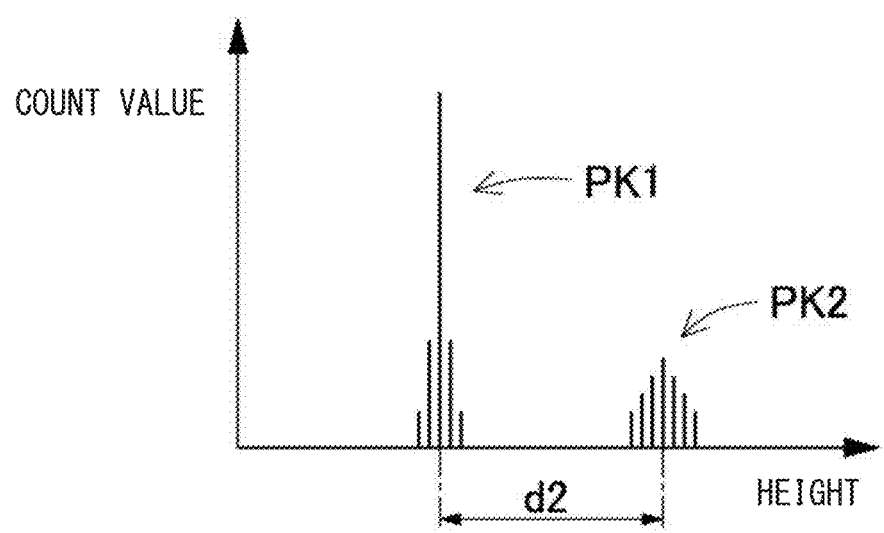
FIG. 20 is a histogram showing distribution of a value of a height of a workpiece.

In setting the reference height such as the reference plane by the reference height setting part 32a, beside the configuration in which the height range for removing the irregularity on the workpiece is directly inputted by the user with numerals from the setting screen displayed in the display part, a configuration may be employed in which an index as a criterion for the setting of the height range is given. For example, a histogram showing distribution of a value of the height of the workpiece as shown in FIG. 20 is displayed in the display part. Here, the histogram is illustrated for the workpiece WK3 in FIGS. 17A to 17G. As to the height value in the planar region in the workpiece WK3, since the count value is considered to be large, it appears as a set of peaks (a first peak set PK1). On the other hand, since the irregular portion on the workpiece WK3 appears as another peak (a second peak set PK2) at a higher position than the first peak set PK1, the height range d is set to a value smaller than a distance d2 between these peaks, which enables the reference height to be set with the irregular portion of the workpiece WK3 excluded.

The designation of the height range can be performed manually from the height range designation part 71 by the user, or can be automatically set. For example, in the histogram showing the distribution of the height value, a region where the most height values are shown is set as the reference height, and based on a standard deviation from this reference height, the height range may be automatically arithmetically operated and designated by the height range designation part or the like.

(Method for Correcting Three-Dimensional Data)

Figure 21:
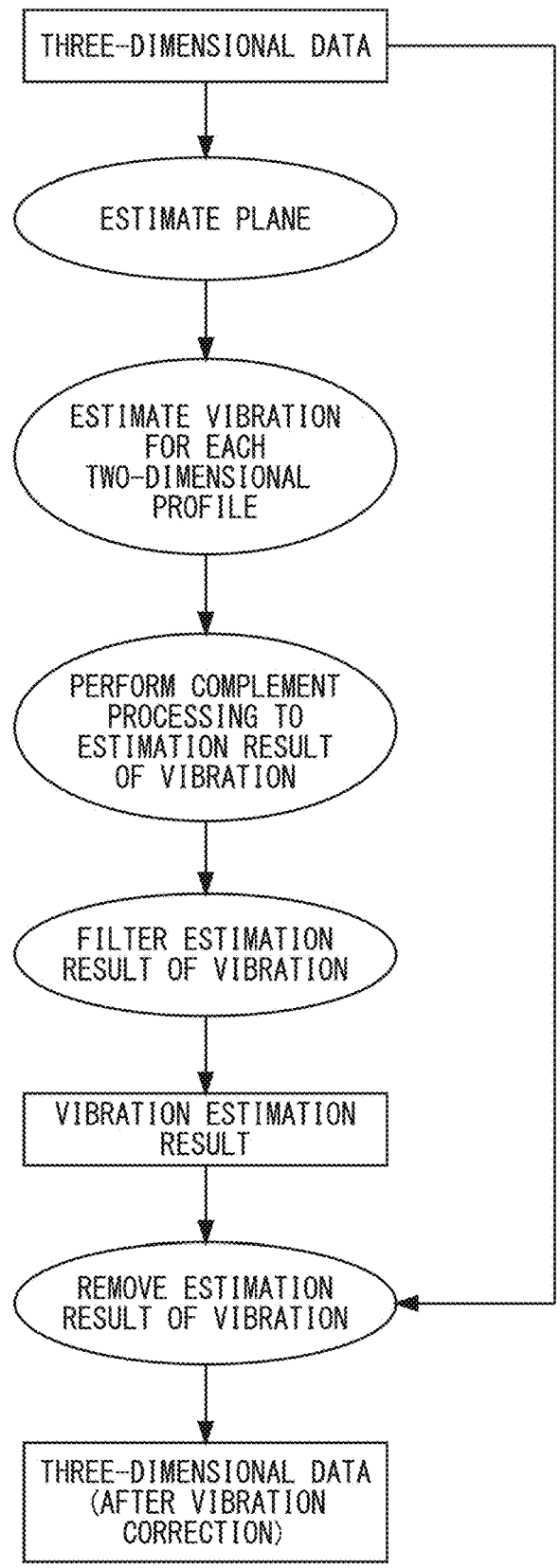
FIG. 21 is a data flow diagram showing how the three-dimensional data after correction in which the vibration component is removed is obtained from the three-dimensional data including the vibration component before the correction.

The above-described procedure for obtaining the three-dimensional date after the correction in which the vibration component is removed from the three-dimensional data before the correction including the vibration component will be described, based on a data flow diagram in FIG. 21. First, the three-dimensional data before the correction including the vibration component is generated from the obtained two-dimensional profiles by the three-dimensional data generation part 32d. Next, the plane is estimated from the obtained three-dimensional data by the reference height setting part 32a. Furthermore, based on the reference plane, the vibration estimation part 32b performs the estimation of the vibration for each of the two-dimensional profiles. Furthermore, the vibration estimation part 32b performs complement processing to the estimation result of the vibration to perform filtering, as needed. By obtaining the estimation result of the vibration in this manner, the vibration component is removed from the three-dimensional data before the correction by the profile correction part 32c, so that the three-dimensional data after the correction not including the vibration component can be obtained.

(Filter Processing)

Figure 22:
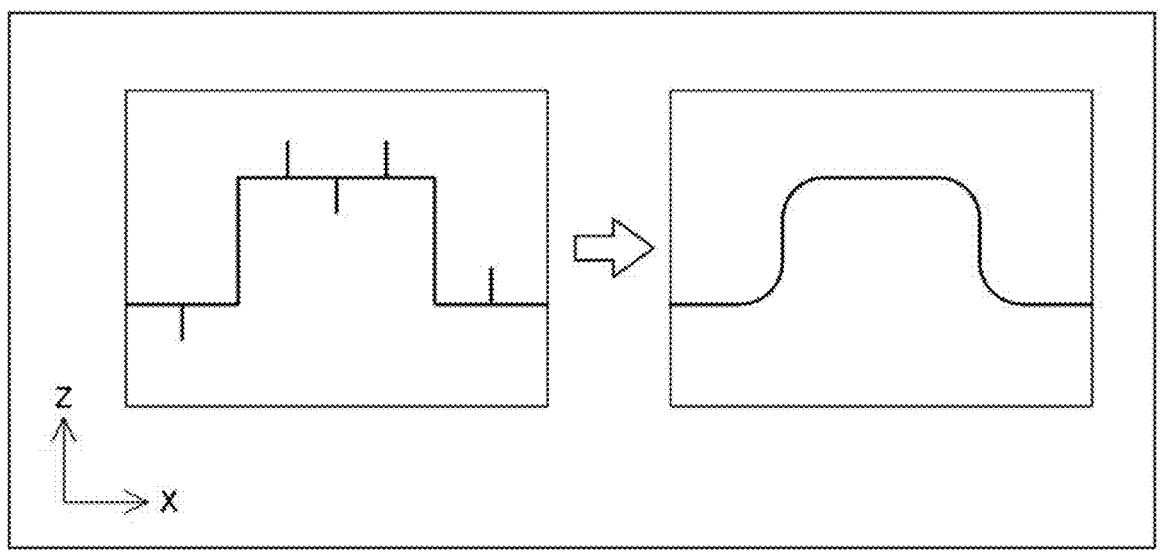
FIG. 22 is a schematic view showing an example in which the two-dimensional profile is subjected to image processing by filter processing.

In the above-described vibration estimation method by the plane correction, it is premised that the plane component exists in the obtained two-dimensional profiles. In this vibration estimation method, if no good-quality plane component exists in the obtained two-dimensional profiles, the estimation of the vibration causes a stable result. Consequently, the two-dimensional profile having a poor straight line fitting degree can be complemented by the reference height setting part 32a, using the vibration estimation results of the adjacent two-dimensional profiles acquired at previous and subsequent timings. Furthermore, the result can also be stabilized, using a Median filter, a Gaussian filter, an averaging filter or a frequency filter. An example in which the two-dimensional profile is subjected to the image processing by the foregoing filter processing is shown in FIG. 22. As shown in this figure, after the two-dimensional profile with large vibration, noise or the like partially caused is made uniform by the filter processing, the plane component can be extracted by the reference height setting part 32a. Moreover, preprocessing may be applied so that a value deviating from an average value is removed as an abnormal value such as noise.

(Reference Plane Designation Part 72)

Figure 23:
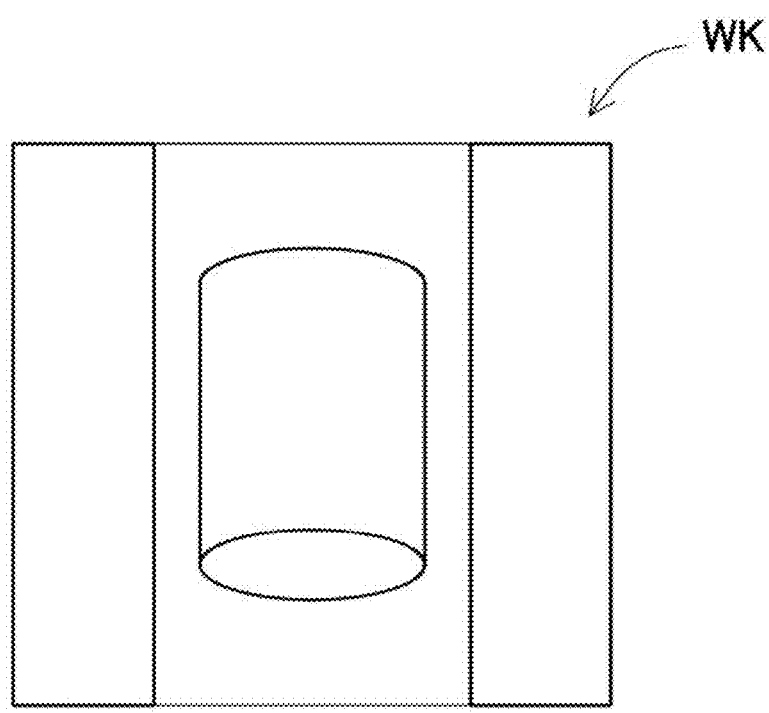
FIG. 23 is a plan view showing how a vibration region is designated with respect to a workpiece having irregularity.

Moreover, beside the configuration in which the reference height setting part 32a automatically calculates the reference plane, a configuration can be employed in which the user manually designates the region as the reference plane. This designation is performed by the reference plane designation part 72 shown in FIG. 3. For example, when the reference height setting part 32a automatically extracts the region as the reference plane from the whole workpiece WK, if a plurality of planes exist and a good plane does not exit, it can be considered that the extraction of the reference plane is not properly performed, and the outer appearance inspection becomes unstable. Consequently, the user directly designates a region that can be sufficiently used as the reference plane, by which the above-described situation can be avoided to stabilize the outer appearance inspection. For example, as to a workpiece WK having irregularity shown in FIG. 23, using the pointing device such as the mouse, the user designates a stable plane as the reference plane while avoiding the irregularity with respect to the height image, which is the three-dimensional data displayed in the three-dimensional data display region 6b of the display part 6. The reference height setting part 32a acquires the reference height by using the region designated by the user as the reference plane.

Beside the configuration in which the user directly designates the reference plane, a configuration may be employed in which the region from which the reference plane is extracted is designated. For example, one or a plurality of regions designated while avoiding a region unsuitable for the reference plane such as a region including irregularity are set as a candidate region(s) of the reference plane from the height image that is a the three-dimensional data displayed on the three-dimensional data display region 6b, and the reference height setting part 32a sets the reference height from the designated candidate region(s). For example, an average height in the designate region(s) is set as the reference height. In this method as well, the setting of the stable reference plane and reference height can be expected, and this method can contribute to accuracy improvement of the outer appearance inspection.

(Mask Region Setting Part 73)

On the contrary, a region not used as the reference plane may be designated by the user. For example, the image inspection device 100 in FIG. 3 includes the mask region setting part 73, and a mask region, which is prohibited from being set as a reference for calculating the reference plane with respect to the height image as the three-dimensional data displayed in the three-dimensional data display region 6b, is designated by the mask region setting part 73. This enables flexible setting in accordance with the workpiece WK and an inspection purpose to be performed by excluding, for example, an irregular portion of the workpiece WK and a region where the vibration easily occurs from the region for obtaining the reference plane and the reference height, and so on.

(Correction Mode Selection Part 74)

Figure 24:
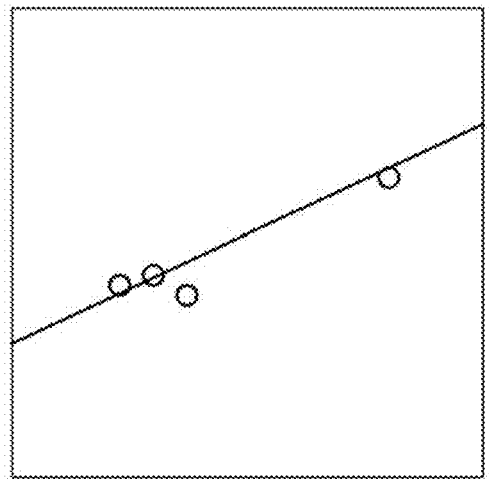
FIG. 24 is a schematic view showing how fitting is performed with a straight line to estimate the rotational vibration with respect to four points configuring the two-dimensional profile.
Figure 25:
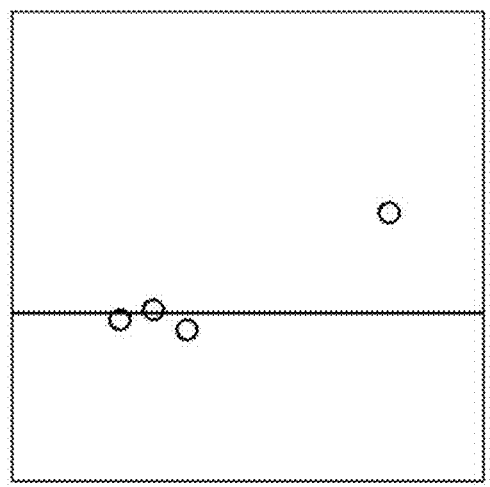
FIG. 25 is a schematic view showing how the fitting is performed with a straight line without correcting the rotational vibration with respect to the four points in FIG. 24.

The above-described modeling of the vibration by the vibration estimation part 32b includes modeling of two types of vibration: vertical vibration and the rotational vibration. Here, in many cases of the image inspection, the vertical vibration is a main component, so that frequently, not performing the modeling of the rotational vibration poses no problem with accuracy. On the other hand, when the estimation of the rotational vibration is performed in addition to the estimation of the vertical vibration, the estimation result of the vibration may be unstable. For example, as shown in FIG. 24, when in an example in which four points are detected in generating the two-dimensional profile, the fitting is performed with a straight line to perform the estimation of the rotational vibration, the reference plane indicated by a straight line in the figure is extracted. In contrast, when the fitting is performed with a horizontal straight line so as to perform only the estimation of the vertical vibration, the reference plane indicated by a straight line in FIG. 25 is extracted, so that the vibration estimation result becomes stable. Consequently, when the vibration estimation part 32b estimates the vibration component, any of a vertical vibration correction mode in which only the vibration component in the height direction is estimated, and a rotational vibration correction mode in which the rotational vibration component around the movement direction is estimated in addition to the vibration component in the height direction is enabled to be selected, which enables the correction of the rotational vibration component to be turned OFF, so that the outer appearance inspection can become stable. This selection of the correction mode is performed by the correction mode selection part 74 shown in FIG. 3. Thereby, in the case where correcting the rotational vibration component makes the outer appearance inspection unstable, correcting only the vertical vibration component can make the outer appearance inspection stable.

Figure 26:
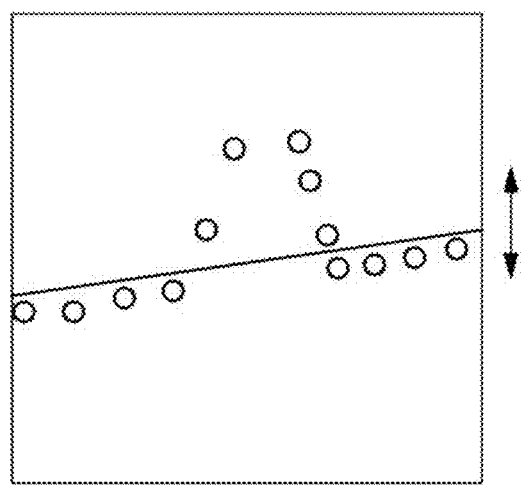
FIG. 26 is a schematic view showing how the reference plane is automatically set with respect to a workpiece having protrusions.
Figure 27:
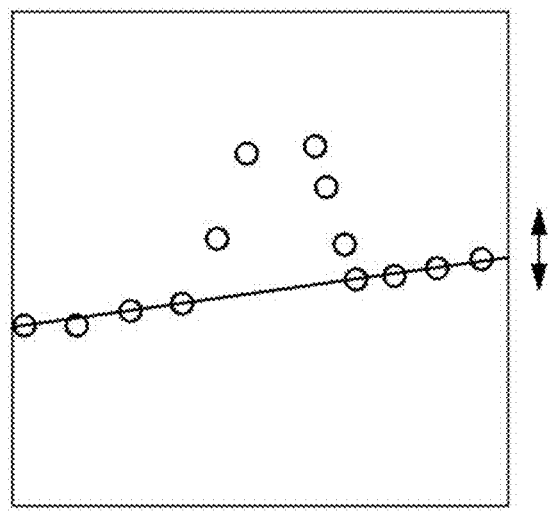
FIG. 27 is a schematic view showing how a component exceeding the height range is excluded to automatically set the reference plane with respect to the two-dimensional profile in FIG. 26.
Figure 28:
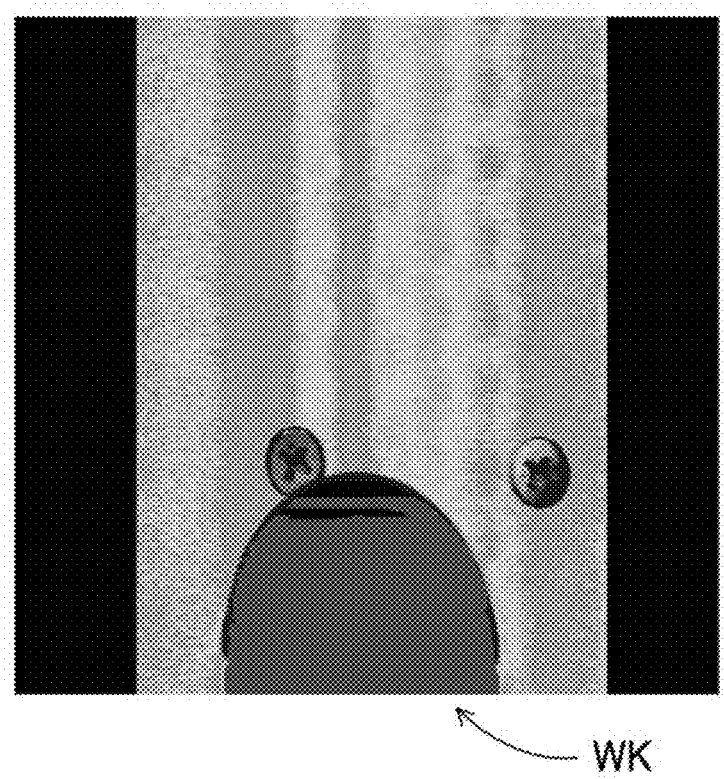
FIG. 28 is an image view showing a height image obtained by automatically extracting the reference plane and removing the vibration component.
Figure 29:
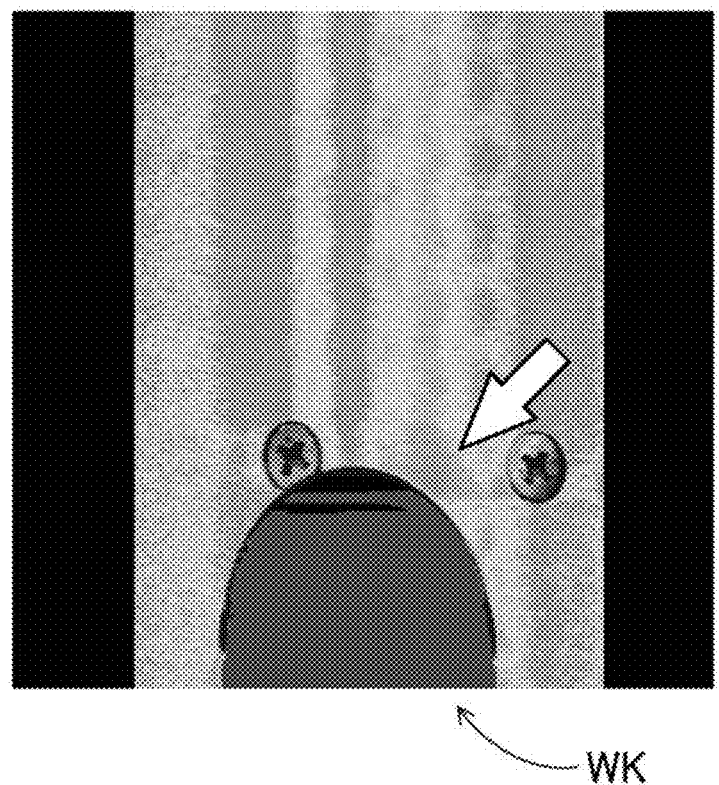
FIG. 29 is an image view showing a height image obtained by designating the height range narrower than that in FIG. 28 to automatically extract the reference plane and removing the vibration component.

Furthermore, in the estimation of the vibration, if the irregularity exists in the surface shape of the workpiece WK, the estimation may be affected by the irregularity. For example, as shown in FIG. 26, when the reference plane is automatically set by the reference height setting part 32a with respect to the workpiece WK having a projected shape in cross-sectional view, it can be considered that respective points of the obtained two-dimensional profile are grasped not as points of the actual workpiece shape but as points moved up and down by the vibration, and the correction is performed by averaging these points to obtain a plane, so that the reference plane deviates from the actual surface of the workpiece WK. Consequently, on the premise that an amplitude of the vibration component is smaller than a height difference of the irregularity in the original shape of the workpiece, the height range for distinguishing the fluctuation due to the vibration component from the height difference of the irregularity of the workpiece is designated, and data having the large height difference is ignored or influence thereof is reduced to set the reference plane. Designating the height difference in the height direction in advance in this manner can reduce the influence on the calculation of the reference height by the presence or absence of the irregularity or the like that the workpiece originally has in the shape of the relevant workpiece. As a result, as shown in FIG. 27, the precise estimation of the vibration component is enabled, in which the points of the two-dimensional profile indicating the original shape of the workpiece, which is not attributed to the vibration component, are excluded. As one example, in the case where the whole image is designated as the reference region as an object of the extraction of the reference plane, the reference plane when the height range is not set or is set to be wide is automatically extracted and the estimation is performed by the vibration estimation part 32b. The vibration component estimated in this manner is removed by the profile correction part 32c to obtain the height image. An example of the obtained height image in the foregoing case is shown in FIG. 28. Moreover, the height range is designated to be narrow, and similarly, the reference plane is automatically extracted, and the vibration opponent is removed by the profile correction part 32c to obtain the height image. An example of the obtained height image in this case is shown in FIG. 29. As be evident from the comparison between these figures, irregularity of the workpiece surface at a portion indicated by arrow in FIG. 29 is maintained in FIG. 29, but is lost in FIG. 28, and it can be understood that the setting of the height range allows the shape of the workpiece WK to be maintained.

The image inspection device 100 includes the height range designation part 71 to designate the height difference in the height direction in the two-dimensional profile as the data that the reference height setting part 32a uses for the calculation of the reference height, as shown in FIG. 3. This allows the reference height setting part 32a to set the reference height, based on the data within the height range designated by the height range designation part 71 in the two-dimensional profiles. The height range can also be regarded as an allowable error to detect as the vibration component. That is, if the allowable error is set to be wide, the large vibration component can be corrected, but influence by the fine irregularity of the workpiece will be received. On the other hand, by setting the allowable error to be small, the above-described influence by the irregularity of the workpiece can become hard to receive. In this manner, in accordance with the size of the amplitude of the vibration component, the height range is set as the allowable error.

(Weighting Processing)

Beside the configuration in which the data deviating from the height range designated by the height range designation part 71 is uniformly ignored to set the reference plane, weighting may be set. For example, the weighting is changed in accordance with how far from the designated height or the like the height of each piece of data is. Specifically, as the height of a point making up the two-dimensional profile becomes farther from the height or the height range designated by the height range designation part 71, the weighting becomes lighter, or as it approaches the designated height or the height range, the weight becomes heavier. Alternatively, for data within a first height range designated by the height range designation part 71, the weighting of 100% may be set, and for the data within a second height range wider than the first height range, the weighting may be changed step by step such that the weighting is varied in accordance with the height. Furthermore, the setting may be made so as to exclude data deviating from the second height range.

Moreover, in the extraction of the reference plane, beside the above-described methods for removing the values outside the above-described predetermined range or reducing the influence, well-known methods for use in association of a local characteristic amount such as a least squares method and a RANSAC (RANDom SAmple Consensus) can also be applied individually or in combination.

Furthermore, a configuration may be employed in which the vibration component is measured, using a vibration meter for use in measurement of physical vibration to specify the vibration component, based on a measured value, and remove the vibration component from the two-dimensional profile by the profile correction part 32c.

Furthermore, beside the configuration in which the reference height setting part 32a sets the reference plane, based on the three-dimensional data before the vibration component is removed, the configuration may be such that the reference plane is set, based on the two-dimensional profile before configuring the three-dimensional data. Especially, since as described above, there are many cases where the correction of the rotational vibration component need not be considered, the extraction of the reference plane as shown in FIG. 27 is enabled, based on the two-dimensional profile at an arbitrary position in the Y-axis direction, or at a position designated by the user.

Alternatively, in the case where after setting the reference plane from the three-dimensional data before the vibration component is removed, the three-dimensional data from which the vibration component is removed is newly generated by the three-dimensional data generation part 32d, beside the configuration in which the vibration component is removed for each of the two-dimensional profiles configuring the three-dimensional data by the profile correction part 32c, a configuration can also be employed in which the profile correction part 32c directly removes the profile of the vibration component with respect to the profiles of the three-dimensional data including the vibration component to correct the three-dimensional data.

Moreover, while in the foregoing, the example in which the reference plane is calculated from the three-dimensional data has been described, the reference height setting part 32a can also set, as the reference height, not only the reference plane but a linear reference line shown in FIG. 27, for example. In this case, the vibration estimation part 32b extracts the vibration component from a difference between the reference line as the reference height and the height of each point of the two-dimensional profile. Alternatively, in place of the plane or the line as the reference height, a point can also be used. In this case, one point or a plurality of points on the three-dimensional data or the two-dimensional profile as the reference height are set as the reference point by the reference height setting part 32a, and, the vibration estimation part 32b extracts the vibration component from a difference in height between the reference point and each point of the two-dimensional profile, in accordance with this reference point.

Figure 30:
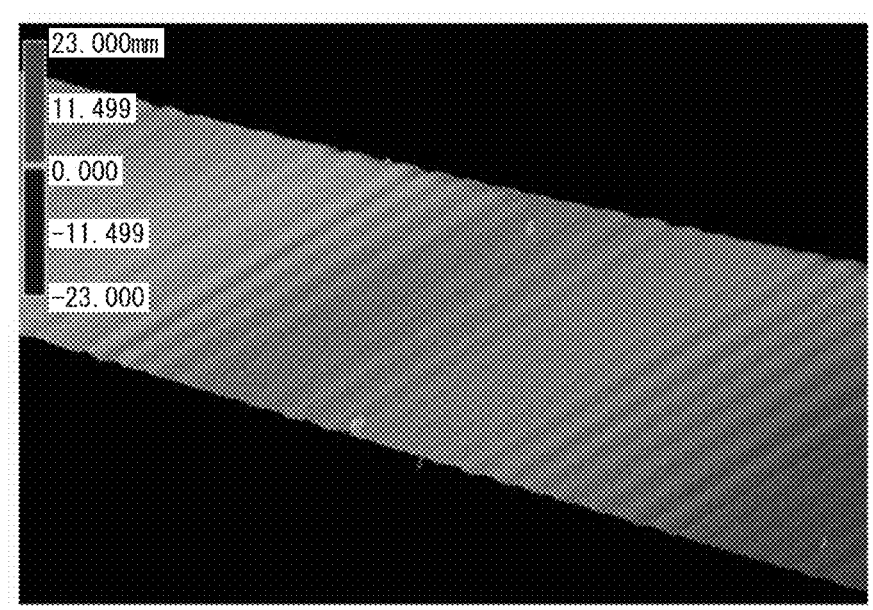
FIG. 30 is an image view showing a height image before the correction obtained by imaging a planar workpiece having projections.
Figure 31:
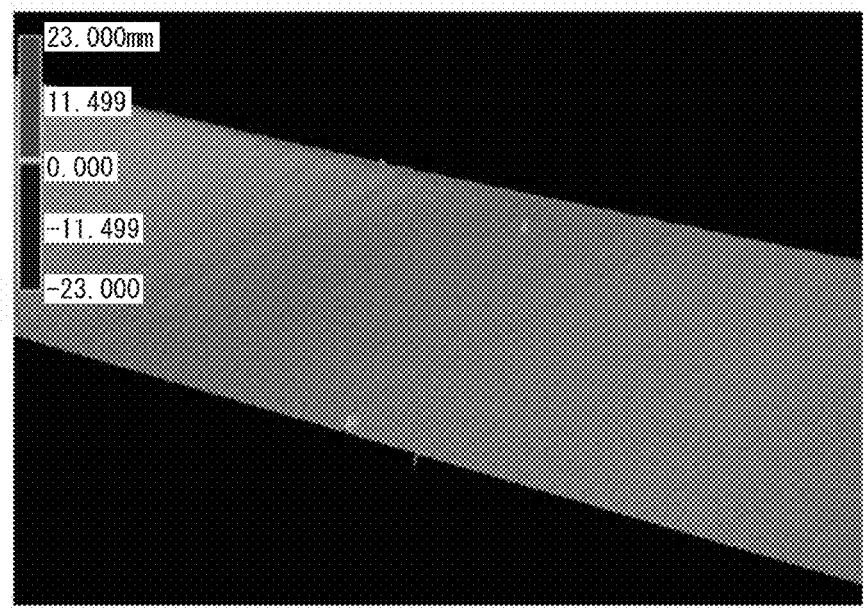
FIG. 31 is an image view showing the height image after the correction in which the vibration component is removed from FIG. 30.

As described above, when scanning the workpiece by the optical cutting method, the image inspection device can correct the vibration component from the three-dimensional data to acquire the height information with the vibration component removed. In this manner, examples of the three-dimensional data after the correction in which the vibration component is removed from the three-dimensional data before the correction are shown in image views of height images in FIGS. 30 to 47. In these views, FIG. 30 shows a height image before the correction obtained by imaging a planar workpiece having two projections in a middle portion, and FIG. 31 shows a height image after the correction in which the vibration component is removed from FIG. 30. In this manner, it is confirmed that in the height image before the correction, a wavy pattern attributed to the vibration component is caused, while in the height image after the correction, a plane with this wavy pattern removed is obtained. Moreover, it is confirmed that the projected portions are properly maintained.

Figure 32:
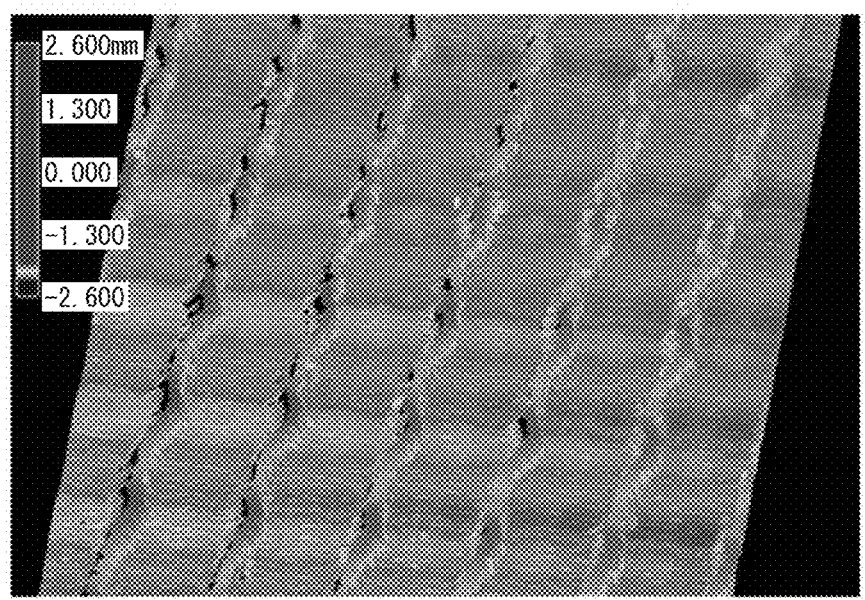
FIG. 32 is an image view showing a height image before the correction obtained by imaging a workpiece having rib-like projections.
Figure 33:
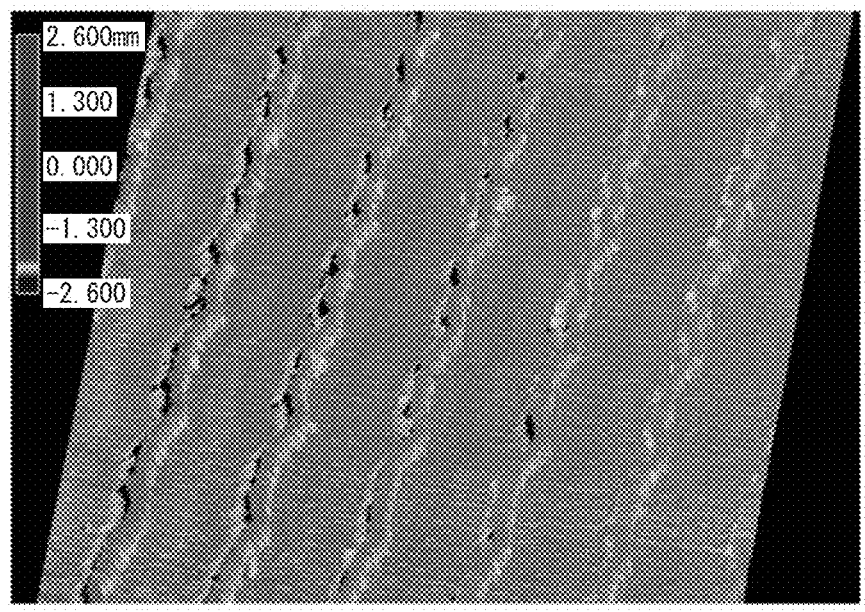
FIG. 33 is an image view showing the height image after the correction in which the vibration component is removed from FIG. 32.

Next, FIG. 32 shows a height image before the correction obtained by imaging a workpiece having rib-like projections along the conveyance direction (the Y-axis direction), and FIG. 33 shows a height image after the correction in which the vibration component is removed from FIG. 32. In this manner, it is confirmed that while a wavy pattern attributed to the vibration component is removed, the projected shape of the workpiece is retained, and only the vibration component is properly removed.

Figure 34:
FIG. 34 is an image view showing a height image before the correction obtained by imaging a workpiece having a flaw.
Figure 35:
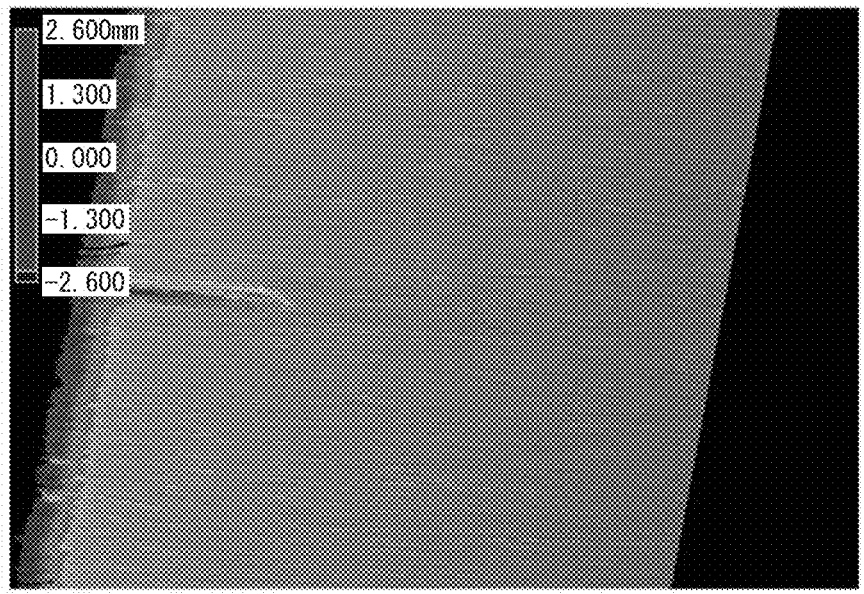
FIG. 35 is an image view showing the height image after the correction in which the vibration component is removed from FIG. 34.

Furthermore, FIG. 34 shows a height image before the correction of a workpiece having a flaw, and FIG. 35 shows a height image after the correction in which the vibration component is removed from FIG. 34. In this manner, it is confirmed that a shape of the flaw is maintained while properly removing a wavy pattern attributed to the vibration component, and that the outer appearance inspection of such a flaw can be properly performed.

Figure 36:
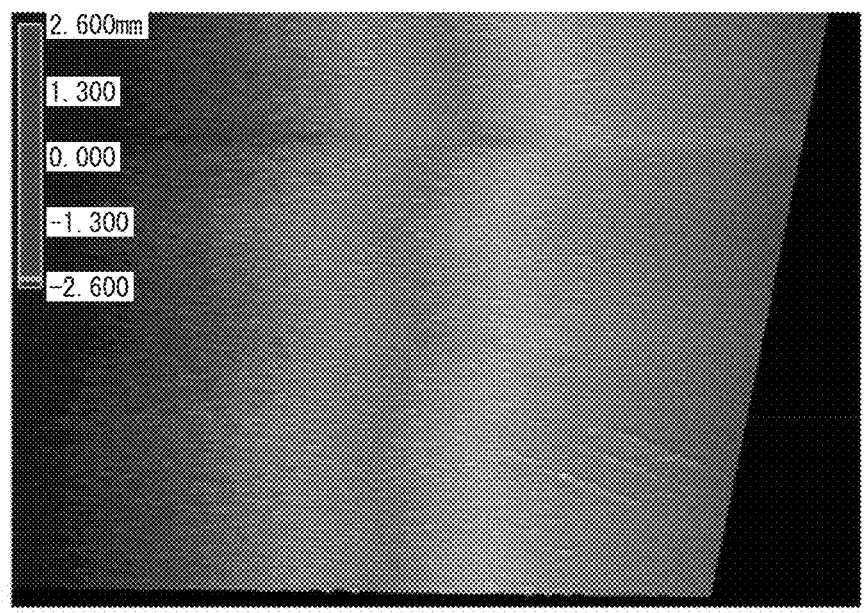
FIG. 36 is an image view showing a height image before the correction obtained by imaging a workpiece to which an impact is applied on the way.
Figure 37:
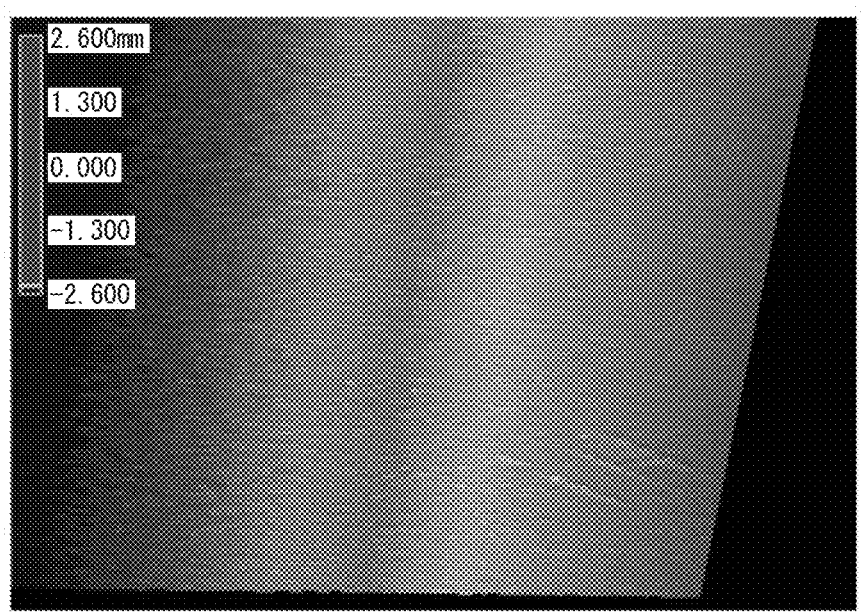
FIG. 37 is an image view showing the height image after the correction in which the vibration component is removed from FIG. 36.

Furthermore, FIG. 36 is a height image before the correction in which an impact is applied on the way, thereby causing a step in this portion, and FIG. 37 shows a height image after the correction in which the vibration component is removed from FIG. 36. In this manner, it can be understood that vibration suddenly caused can also be properly removed by the vibration correction function.

Figure 38:
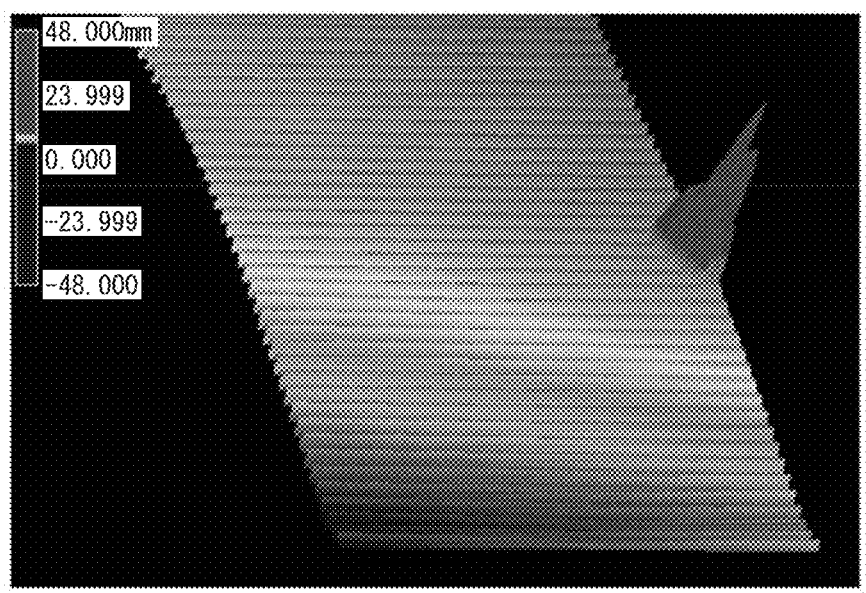
FIG. 38 is an image view showing a height image before the correction obtained by imaging a workpiece having a projection and disposed obliquely.
Figure 39:
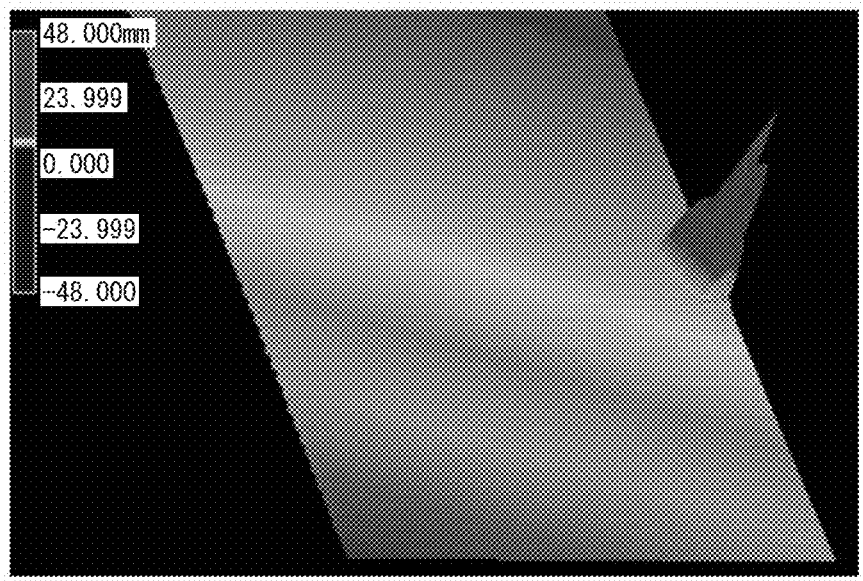
FIG. 39 is an image view showing the height image after the correction in which the vibration component is removed from FIG. 38.

Furthermore, FIG. 38 shows a height image before the correction in which a workpiece partially having a projection is disposed obliquely, and FIG. 39 shows a height image after the correction in which the vibration component is removed from FIG. 38. In this manner, it can be confirmed that only a wavy pattern attributed to the vibration component can be properly removed while maintaining an inclination posture of a plane and maintaining the projection.

Figure 40:
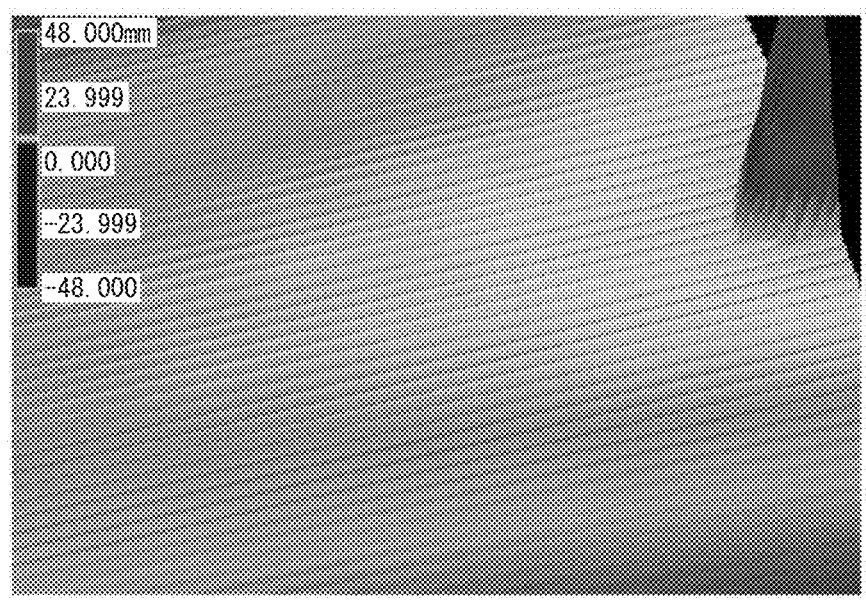
FIG. 40 is an image view showing a height image before the correction obtained by imaging a workpiece having a projection.
Figure 41:
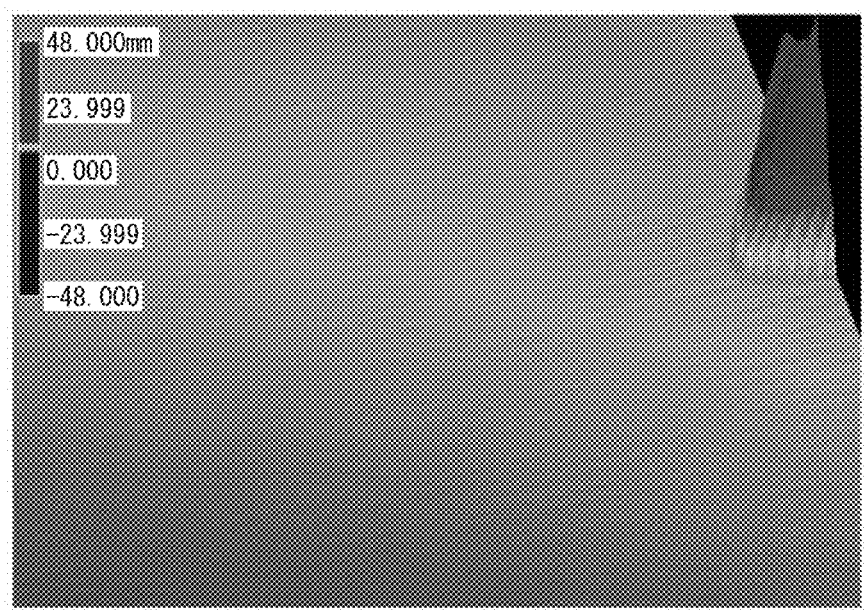
FIG. 41 is an image view showing the height image after the correction in which the vibration component is removed from FIG. 40.

Further, FIG. 40 shows a height image before the correction of a workpiece similarly having a projection, and FIG. 41 shows a height image after the correction in which the vibration component is removed from FIG. 40. In this manner, it can be confirmed that only the above-described vibration component can be properly removed even if the vibration component is not uniform, and amplitude partially differs.

Figure 42:
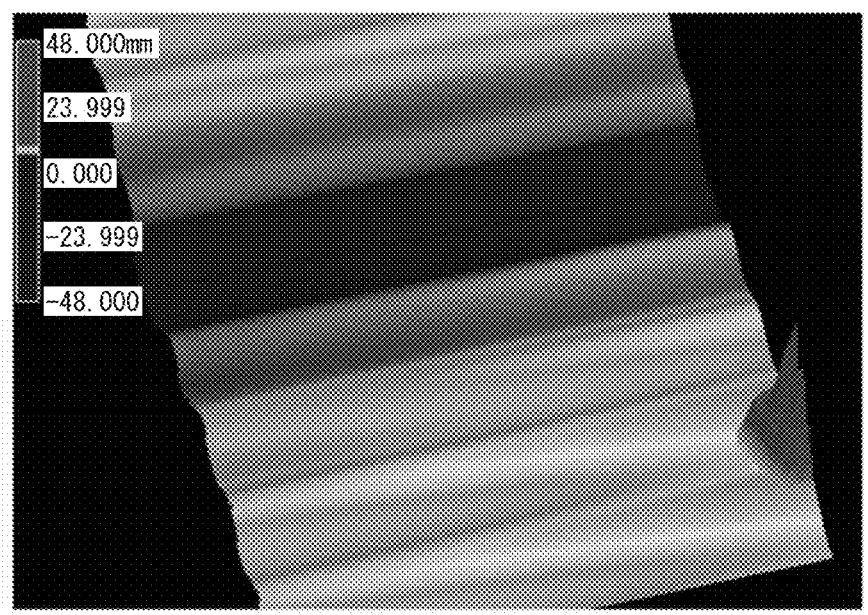
FIG. 42 is an image view showing a height image before the correction obtained by imaging a workpiece having a projection.
Figure 43:
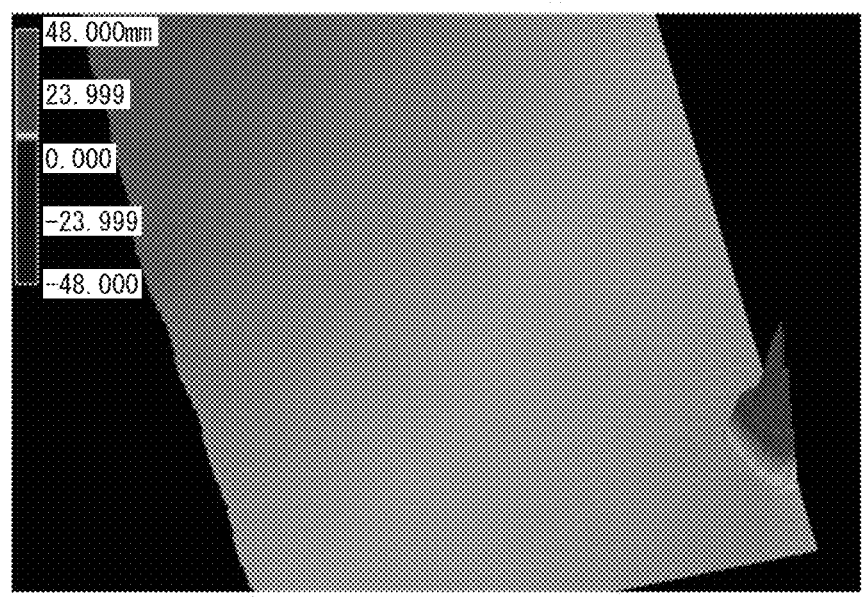
FIG. 43 is an image view showing the height image after the correction in which the vibration component is removed from FIG. 42.

Furthermore, FIG. 42 shows a height image before the correction of a workpiece similarly having a projection, and FIG. 43 shows a height image after the correction in which the vibration component is removed from FIG. 42. Here, it can also be confirmed that only the above-described vibration component can be properly removed even in the case of the non-uniform vibration component having varied pitches and having partially varied height of irregularity.

Figure 44:
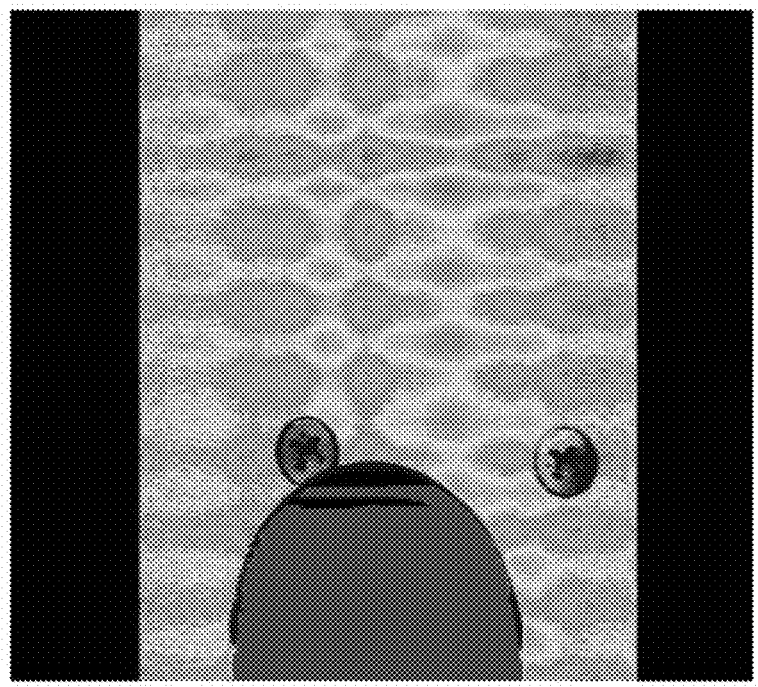
FIG. 44 is an image view showing a height image before the correction obtained by imaging a workpiece with a screw head and table-tennis balls disposed.
Figure 45:
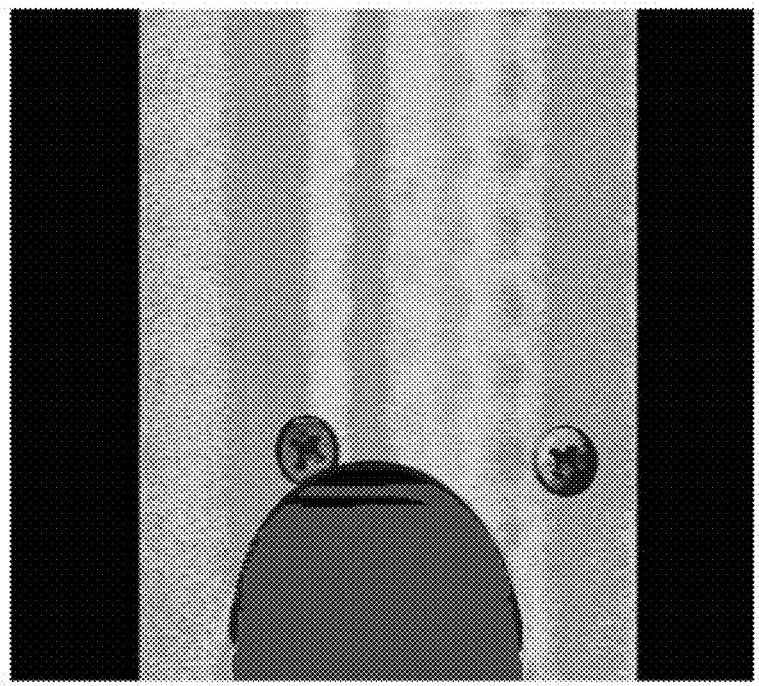
FIG. 45 is an image view showing the height image after the correction in which the vibration component is removed from FIG. 44.

Furthermore, FIG. 44 shows a height image before the correction of a workpiece with a screw head and table-tennis balls disposed on a plane, and FIG. 45 shows a height image after the correction in which the vibration component is removed from FIG. 44. In this manner, it can be confirmed that only the vibration component can be properly removed while maintaining the irregularity shapes of the workpiece even if the portions largely different in height exist in the workpiece.

Figure 46:
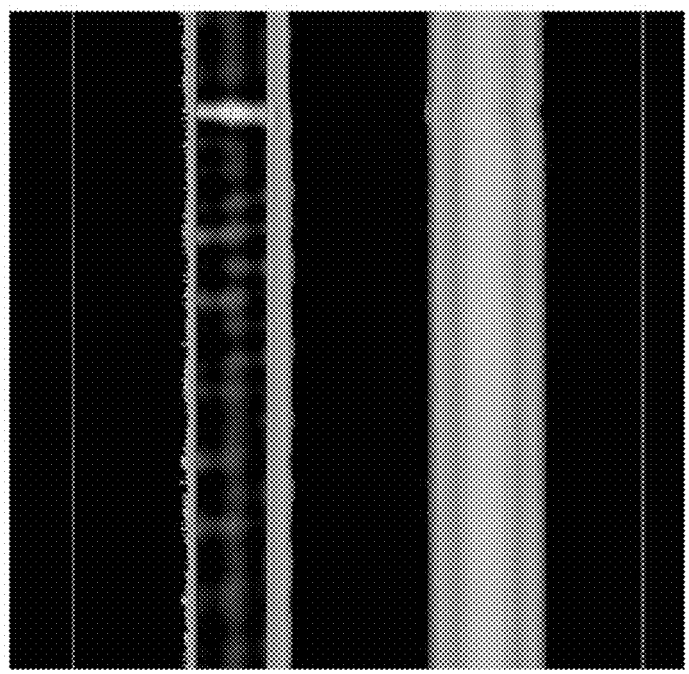
FIG. 46 is an image view showing a height image before the correction obtained by imaging cable-like workpieces along a periphery.
Figure 47:
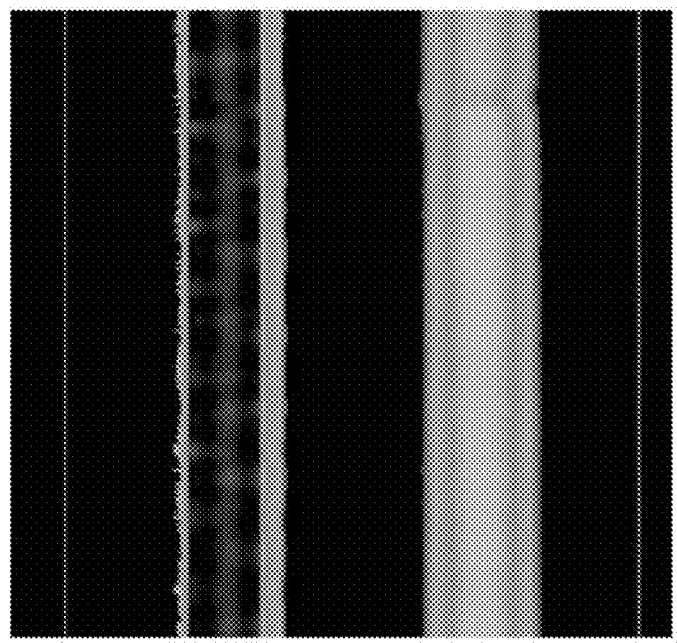
FIG. 47 is an image view showing the height image after the correction in FIG. 46.

In the foregoing, the examples in which the vertical vibration component is removed have been described. Finally, an example in which the rotational vibration component is removed is shown in FIGS. 46 and 47. In these figures, FIG. 46 shows a height image before the correction obtained by imaging cable-like workpieces along a periphery, and FIG. 47 shows a height image after the correction of FIG. 46. It is confirmed that the vibration component appearing spaced in a horizontal direction can be removed by the correction in FIG. 47.

In this manner, the vibration component can be easily removed by the arithmetical operation without introducing an expensive antivibration mechanism or a clamp mechanism for the workpiece. As a result, problems of costs and man-hours, which have been barriers to introduction of the image inspection device, can be reduced.

Moreover, the reference height setting part arithmetically operates the reference height individually for each workpiece. That is, since when the workpiece is newly conveyed, the two-dimensional profiles and the height image of this workpiece are acquired, the reference height is also updated in accordance with the update of this three-dimensional data or the like. At this time, a configuration may be employed in which the reference height is varied with reference to the reference height used before. Especially, in an aspect in which workpieces having similar shapes are sequentially inputted, beside the arithmetical operation of the reference height every time, only a difference can be arithmetically operated to simplify the processing.

Furthermore, beside the estimation of the vibration component with respect to the acquired two-dimensional profiles, a configuration may be employed in which using an interlace system, the vibration estimation part estimates the vibration component with respect to the two-dimensional profiles not adjacent and discretely located while skipping over one or a plurality of two-dimensional profiles, and for the skipped two-dimensional profiles, the correction data is generated and addressed by complementation without performing the arithmetical operation. The above-described configuration allows acceleration of processing time to be expected.

As described above, as the image inspection device, the example using the height image obtained by composing the two-dimensional profile images obtained by the optical cutting method as shown in FIGS. 4A to 4C has been described. However, in the invention, the method for acquiring the height image is not limited to this method, but a well-known method that enables the height information to be acquired can be employed as needed. Examples of methods using the principle of triangulation include a stripe projection image method, a phase shift method, a space coding method, a random pattern projection method, beside the optical cutting method. Moreover, examples of non-contact active three-dimensional measurement methods using other than the principle of triangulation include a Time of Flight (TOF) method, a confocal method, and the like. Alternatively, examples of a non-contact passive three-dimensional measuring method include a focal method such as a stereo method (a stereo method after calibration or photogrammetry), a lens focal method.

(Head Conveyance Mechanism)

Figure 48:
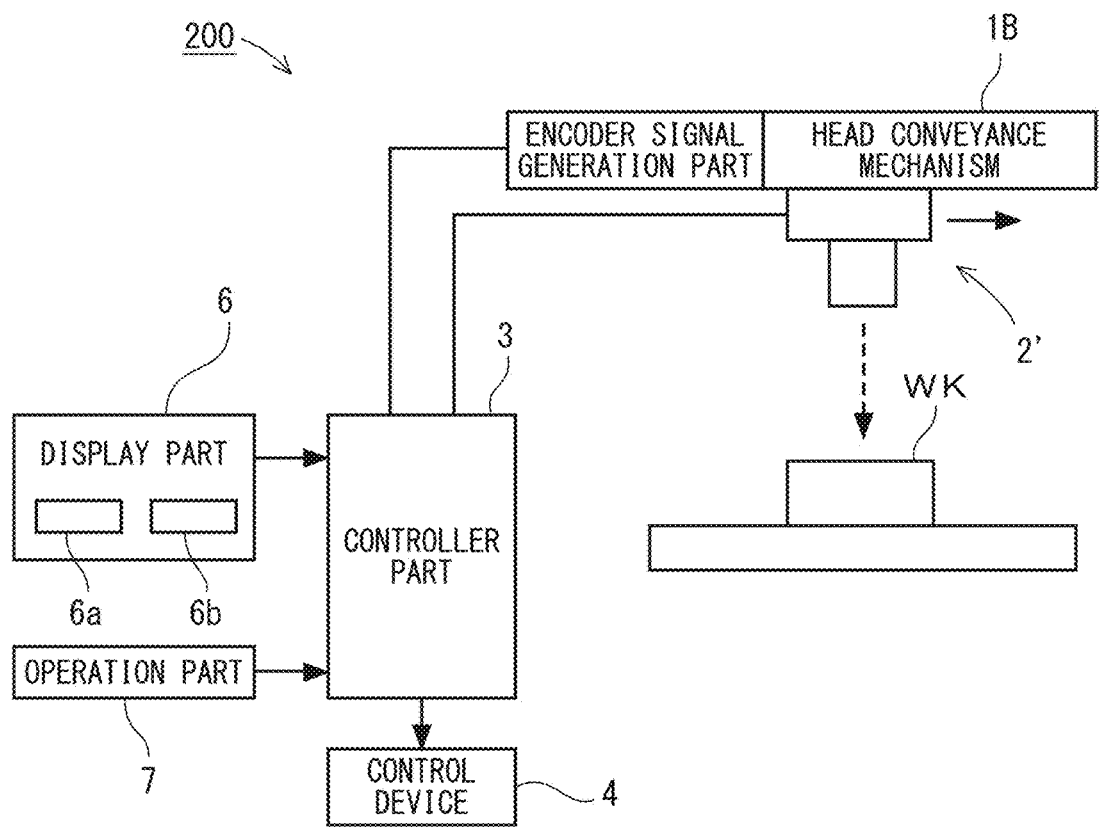
FIG. 48 is a schematic view showing a configuration in which a head part side is moved relatively to a workpiece in a three-dimensional image inspection device according to a second embodiment.

Moreover, in the foregoing, the example has been described, in which as shown in FIGS. 1 and 2, the outer appearance inspection of the workpiece WK is conducted in the configuration of fixing the side of the head part 2 as the camera, (exactly, the detection part 22) and conveying the workpiece WK by the workpiece conveyance mechanism 1 to relatively move the head part 2 and the workpiece WK. However, the invention is not limited to this configuration, but the head part side can be caused to perform scanning. For example, as in an image inspection device 200 according to a second embodiment shown in FIG. 48, a workpiece WK side is made stationary, and a head part 2' is moved relatively to a workpiece WK by a head conveyance mechanism 1B to scan a surface of the workpiece WK, by which two-dimensional profiles of the workpiece WK can be sequentially acquired to compose three-dimensional data. In this movement form as well, vibration occurs in the head conveyance mechanism 1B, and this may affect accuracy of the outer appearance inspection, and thus, estimation and correction of the vibration can be applied in a similar method. Moreover, the workpiece does not need to be fixed, and a configuration may be such that the head part side is also caused to perform scanning while conveying the workpiece. In this manner, the invention can be applied to the configuration in which the workpiece and the detection part of the head part are relatively moved in order to estimate and remove the vibration component.

An image inspection device, an image inspection method, an image inspection program, and a computer-readable recording medium and recording equipment of the invention can be utilized for outer appearance inspection of a workpiece conveyed on a line.

What is claimed is:

1. An image inspection device for conducting outer appearance inspection, based on height information of an inspection object, the image inspection device comprising:
   an irradiation part configured to apply measurement laser light to the inspection object relatively moved in one direction, wherein the irradiation part is a light projecting element that emits a laser beam;
   a detection part configured to detect reflected light that is applied from the irradiation part to the inspection object and is reflected at the inspection object, the reflected light including a vibration component in a height direction;
   a head part to generate a plurality of two-dimensional profiles indicating a cross-sectional shape of the inspection object at predetermined intervals, based on detection data obtained by the detection part;
   a three-dimensional data generation part configured to obtain a height image as a three-dimensional data by composing the plurality of two-dimensional profiles;
   a height range designation part from a setting screen on a display part to designate a height difference in the height direction in the two-dimensional profile;
   a reference height setting part configured to extract data in a height range set by the height range designation part and set a reference height plane as a reference of vibration component estimation, based on the extracted three-dimensional data before the vibration component obtained from a plurality of the two-dimensional profiles is removed, wherein the height difference outside the height range is excluded from a basis of calculation of the reference height plane;
   a vibration estimation part configured to estimate the vibration component in an inspection environment, based on the two-dimensional profile generated by the two-dimensional profile generation part and the reference height set by the reference height setting part, wherein the vibration estimation part estimates the vibration component from a difference between the reference height and each of the two-dimensional profiles and the estimation of the vibration component is performed for each of the two-dimensional profiles;
   a profile correction part configured to remove, from each of the two-dimensional profiles, the vibration component estimated by the vibration estimation part;
   wherein the three-dimensional data generation part reconstructs the three-dimensional data of the inspection object from the plurality of two-dimensional profiles from which the vibration component is removed by the profile correction part; and an inspection part configured to conduct the outer appearance inspection of the inspection object, based on the three-dimensional data generated by the three-dimensional data generation part.

2. The image inspection device according to claim 1, wherein the reference height setting part estimates a planar reference plane as the reference height, based on the three-dimensional data before the vibration component is removed, the three-dimensional data having been generated by the three-dimensional data generation part, and the vibration estimation part estimates the vibration component of each of the two-dimensional profiles, based on a reference straight line obtained from a cross section of the reference plane estimated by the reference height setting part, and a height on the two-dimensional profile corresponding to the estimated reference straight line.

3. The image inspection device according to claim 1, wherein the reference height setting part estimates a reference curved plane as the reference height, based on the three-dimensional data before the vibration component is removed, the three-dimensional data having been generated by the three-dimensional data generation part, and the vibration estimation part estimates the vibration component of each of the two-dimensional profiles, based on a reference curved line obtained from a cross section of the reference curved plane estimated by the reference height setting part, and a height on the two-dimensional profile corresponding to the estimated reference curved line.

4. The image inspection device according to claim 3, wherein the reference height setting part automatically sets the reference plane, based on the three-dimensional data before the vibration component is removed.

5. The image inspection device according to claim 2, further comprising a reference plane designation part from a setting screen on a display part configured to designate: a three-dimensional data display region to display the three-dimensional data before the vibration component is removed; and a region as the reference plane in the three-dimensional data displayed in the three-dimensional data display region.

6. The image inspection device according to claim 2, further comprising a mask region setting part from a setting screen on a display part configured to set a mask region that the reference height setting part is prohibited from setting as the reference for calculating the reference plane from the three-dimensional data before the vibration component is removed.

7. The image inspection device according to claim 2, wherein the reference height setting part sets the reference height, based on the three-dimensional data before the vibration component is removed, the vibration estimation part estimates the vibration component in the height direction from a relationship between the reference straight line and the two-dimensional profile, and the profile correction part performs the correction.

8. The image inspection device according to claim 7, wherein the reference height setting part sets the reference height based on the three-dimensional data before the vibration component is removed, the vibration estimation part estimates the vibration component in the height direction and the vibration component around a rotation axis in a movement direction of the inspection object from a relationship between the reference straight line and the two-dimensional profile, and the profile correction part performs the correction.

9. The image inspection device according to claim 1, wherein the reference height setting part varies the reference height with reference to the reference height used in the past.

10. The image inspection device according to claim 3, wherein the reference height setting part calculates one reference profile from the plurality of two-dimensional profiles configuring the three-dimensional data before the vibration component is removed, and the vibration estimation part estimates the vibration component, based on the reference profile and the height of the two-dimensional profile corresponding to the reference profile.

11. The image inspection device according to claim 10, wherein the reference height setting part filters the plurality of two-dimensional profiles in a scanning direction of the inspection object to calculate the one reference profile, and the vibration estimation part estimates the vibration component of the two-dimensional profile, based on the calculated reference profile.

12. The image inspection device according to claim 10, wherein the reference height setting part calculates the reference profile, based on the plurality of two-dimensional profiles acquired at adjacent positions, and the vibration estimation part estimates the vibration component of the two-dimensional profile, based on the calculated reference profile.

13. The image inspection device according to claim 10, wherein the reference profile is a planar portion in an outer shape of the inspection object.

14. The image inspection device according to claim 1, wherein the vibration estimation part skips over one or more two-dimensional profiles to select the two-dimensional profiles, and estimates the vibration component with respect to the selected two-dimensional profiles, and further complements correction data of the obtained vibration component with respect to the two-dimensional profiles between the selected two-dimensional-profiles.

15. The image inspection device according to claim 14, wherein the vibration estimation part calculates the vibration component, based on the two-dimensional profile having height data in which a difference from the reference height set by the reference height setting part is within a predetermined range.

16. The image inspection device according to claim 15, wherein the vibration component in a portion having the height data outside the predetermined range is complemented, using an estimation result of the vibration component in a periphery of the portion.

17. The image inspection device according to claim 1, further comprising a correction mode selection part from a setting screen on a display part configured to select any of:

a vertical vibration correction mode in which the vibration estimation part estimates the vibration component in the height direction as the vibration component; and a rotational vibration correction mode in which the vibration estimation part estimates a rotational vibration component around the movement direction in addition to the vibration component in the height direction.

18. An image inspection method for conducting outer appearance inspection, based on height information of an inspection object, the method comprising the steps of:

applying measurement laser light to the inspection object relatively moved in one direction, and detecting reflected light that is reflected at the inspection object, and includes a vibration component in a height direction;

generating a plurality of two-dimensional profiles indicating a cross-sectional shape of the inspection object at predetermined intervals, based on the detected detection data;

obtaining a height image as a three-dimensional data by composing the plurality of two-dimensional profiles;

setting a height difference in a height direction in the two-dimensional profile;

setting a reference height plane as a reference of vibration component estimation, based on the generated two-dimensional data, wherein the height difference outside a height range is excluded from a basis of calculation of the reference height plane;

estimating the vibration component in an inspection environment, based on the generated two-dimensional profile and the set reference height, wherein the vibration component is estimated from a difference between the reference height and each of the two-dimensional profiles and the estimating is performed for each of the two-dimensional profiles;

removing the estimated vibration component from the two-dimensional profile;

generating three-dimensional data of the inspection object from a plurality of the two-dimensional profiles from which the vibration component is removed; and conducting the outer appearance inspection of the inspection object, based on the generated three-dimensional data.

* * * * *